United States Patent
Sailor et al.

(10) Patent No.: US 7,482,168 B2
(45) Date of Patent: Jan. 27, 2009

(54) PHOTOLUMINESCENT POLYMETALLOLES AS CHEMICAL SENSORS

(75) Inventors: Michael J. Sailor, La Jolla, CA (US); William C Trogler, Del Mar, CA (US); Honglae Sohn, Gwangju (KR); Rebecca M. Calhoun, Austin, TX (US)

(73) Assignee: The Regents of the University of California, Oakland, CA (US)

( * ) Notice: Subject to any disclaimer, the term of this patent is extended or adjusted under 35 U.S.C. 154(b) by 232 days.

(21) Appl. No.: 10/244,053

(22) Filed: Sep. 14, 2002

(65) Prior Publication Data

US 2005/0101026 A1    May 12, 2005

Related U.S. Application Data

(60) Provisional application No. 60/322,908, filed on Sep. 15, 2001.

(51) Int. Cl.
*G01N 33/00* (2006.01)
*G01N 21/76* (2006.01)

(52) U.S. Cl. ..................... 436/172; 436/106

(58) Field of Classification Search ............... 436/106, 436/107, 110, 156, 172; 250/458.1, 459.1
See application file for complete search history.

(56) References Cited

U.S. PATENT DOCUMENTS 6,169,193 B1 *   1/2001   West et al. ............... 556/406

FOREIGN PATENT DOCUMENTS

WO          2004/058841   *   7/2004

OTHER PUBLICATIONS

Yamaguchi, S. et al "Toward New Materials for Organic Electroluminescent Devices: Synthesis, Structures, and Properties of a Series of 2,5-Diaryl-3,4-diphenylsiloles" Chem. Eur. J., vol. 6 (2000) pp. 1683-1692, no month.*

Mullin, J. et al "Photochemical behavior of Group-14 metalloles" Abstracts of Papers, 221st ACS National Meeting, San Diego, CA, Apr. 1-5, 2001 INOR-459.*

Sohn, H. et al "Detection of TNT and picric acid onsurfaces and in seawater using photoluminescent polymers containing group IV metalloles" Abstracts of Papers, 221st ACS National Meeting, San Diego, CA, Apr. 1-5, 2001 INOR-589.*

Trogler, W. et al "Luminescent polysilole and polygermole sensors for TNT" Abstracts of Papers, 225th ACS National Meeting, New Orleans, LA, Mar. 23-27, 2001 INOR-746.*

(Continued)

*Primary Examiner*—Jill Warden
*Assistant Examiner*—Timothy G Kingan
(74) *Attorney, Agent, or Firm*—Greer, Burns & Crain, Ltd.

(57) ABSTRACT

A method to develop inexpensive inorganic polymeric sensors that can provide a sensitivity and selectivity for explosive nitroaromatic compounds. Selectivity is provided by the arrays of 12 different reactive fluorescent sensors to mimic the human olfactory system. The sensors are based on photoluminescence quenching of polymers containing metalloid-metalloid backbones such as Si—Si, Si—Ge, or Ge—Ge. The sensor employs a thin film of photoluminescent copolymers, which is stable in air, water, acids, common organic solvents, and even seawater containing bioorganisms. The detection method involves measurement of the quenching of photoluminescence of the polysilole by the analyte.

22 Claims, 23 Drawing Sheets

OTHER PUBLICATIONS

Sohn, H. et al "Detection of Nitroaromatic Explosives Based on Photoluminescent Polymers Containing Metalloles" J. Amer. Chem. Soc. vol. 125 (2003) pp. 3821-3830, no month.*

Sohn, H. et al "Detection of TNT and picric acid on surfaces and in seawater by using photoluminescent polysiloles" Chemical Abstracts, vol. 135, (2001) abstract No. 141846, no month.*

Albert, K. J., Myrick, M. L., Brown, S. B., James, D. L., Milanovich, F. P., Walt, D. R., "Field-Deployable Sniffer for 2, 4-Dinitrotoluene Detection.," Environ. Sci. Technol. 2001, 35, 3193-3200.

Albert, K. J., Lewis, N. S., Schauer, C. L., Sotzing, G. A., Stitzel, S. E., Vaid, T. P., Walt, D. R., "Cross-Reactive Chemical Sensor Arrays," 2000, Chem. Rev., 100, 2595-2626.

Anferov, V. P., Mozjoukhine, G. V., Fisher, R., "Pulsed Spectrometer for Nuclear Quadrupole Resonance for Remote Detection of Nitrogen in Explosives," Apr. 2000, Rev. Sci. Instrum.. 71, No. 4, 1656-1659.

Bankwitz, U., Sohn, H., Powell, D. R., West, R. J., "Synthesis, Solid-State Structure, and Reduction of 1, 1-Dichloro-2,3,4,5-Tetramethylsilole," 1995, Journal of Organomet. Chem., 1995, 499, C7-C9.

Barshick, S.-A., "Analysis of Accelerants and Fire Debris Using Aroma Detection Technology" 1998, J. Forensic Sci., 43, 284-293.

Content, S., Trogler, W. C., Sailor, M. J., "Detection of Nitrobenzene, DNT, and TNT Vapors by Quenching of Porous Silicon Photoluminescence" 2000, Chem. Eur. J., 6, 2205-2213.

Czarnik, A. W., "A Sense for Landmines," Nature, Jul. 30, 1998, 394, 417-418.

Fainberg, A., "Explosives Detection for Aviation Security," Science, Mar. 20, 1992, 255, 1531-1537.

Freeman, W. P., Tilley, T. D., Yap, G. P. A, Rheingold, A L., "Silolyl Anions and Silole Dianions: Structure of $[K([18]crown-6)^+]_2[C_4Me_4Si^{2-}]$," Angew. Chem. Int. Ed. Engl., 1996, 35, 882-884.

Grinvald, A., Steinberg, I. Z., "On the Analysis of Fluorescence Decay Kinetics by the Method of Least-Squares," Analytical Biochem., 1974, 59, 583-598.

Hakansson, K, Coorey, R. V., Zubarev, R. A., Talrose, V. L., Hakansson, P., "Low-mass Ions Observed in Plasma Desorption Mass Spectrometry of High Explosives," J. Mass Spectrom, 2000, 35, 337-346.

Hong, J. H., Boudjhouk, P., Castellino, S., "Synthesis and Characterization of Two Aromatic Silicon-Containing Dianions: The 2,3,4,5-Tetraphenylsilole Dianion and the 1,1'-Disila-2,2'3,3'4,4'5,5'-Octaphenylfulvalene Dianion," Organometallics, 1994, 13, 27.

Kanno, K., Ichinohe, M., Kabuto, C., Kira, M., "Synthesis and Structure of a Series of Oligo[1,2-(2,3,4,5-tetramethylsilole)]s," Chem. Lett. 1998, 99-100.

Krausa, M., Schorb, K., "Trace Detection of 2,4,6-trinitrotoluene in the Gaseous Phase by Cyclic Voltammetry" J. Electroanalytical Chem., 1999, 461, 10-13.

Laws, W. R, Potter, D. W., Sutherland, J. C., "Gating Circuit for Single Photon-Counting Flourescence Lifetime Instruments Using High Repetition Pulsed Light Sources," Rev, Sci. Instrum, Oct. 1984, 55, 1564-1568.

Liu, Y., Mills, R C., Boncella, J. M., Schanze, K. S., "Fluorescent Ployacetylene Thin Film Sensor for Nitroatomatics," Langmuir, 2001, 17, 7452-7455.

Lu, J., Zhang, Z., "A Reusable Optical Sensing Layer for Picric Acid Based on the Luminescence Quenching of the Eu-Thenoyltrifluoroacetone Complex," Analytica Chimica Acta, 1996, 318, 175-179.

Luggar, R. D., Farquharson, M. J., Horrocks, J. A., Lacey, R. J., "Multivariate Analysis of Statistically Poor EDXRD Spectra for the Detection of Concealed Explosives," X-ray Spectrometry 1998, 27, 87-94.

Magde, D., Campbell, B. F., "Improved Methodology for Time-Correlated Single Photon Counting," SPEI, 1989, 1054, 61-68.

Marquardt, D. W., "An Algorithm for Least-Squares Estimation of Nonlinear Parameters," J. Soc. Indust. Appl. Math, 1963, 11, 431-441.

McGill, R. A, Mlsna, T. E., Mowery, R., "The Design of Functionalized Silicone Ploymers for Chemical Sensor Detection of Nitroaromatic Compounds," IEEE International Frequency Control Symposium, 1998, pp. 630-633.

McQuade, D. T., Pullen, A E., Swager, T. M., "Conjugated Polymer-Based Chemical Sensors," Chem. Rev., 2000, 100, 2537-2574.

Rouhi, A. M., "Land Mines: Horrors Begging for Solutions," Chem. Eng. News, 1997, 75, 14-22.

Sanji, T., Sakai, T., Kabuto, C., Sakurai, H., "Silole-Incorporated Polysilanes" J. Am. Chem. Soc., 1998, 120, 4552-4553.

Shriver-Lake, L. C., Donner, B. L., Ligler, F. S., "On-Site Detection of TNT with a Portable Fiber Optic Biosensor," Environ. Sci. Technol., 1997, 31, 837-841.

Sillen, A., Engelboroughs, Y., "The Correct Use of "Average" Fluorescence Parameters," Photochem. and Photobiol., 1998, 67, 475-486.

Sylvia, J. M., Janni, J. A., Klein, J. D., Spencer, K. M., "Surface-Enhanced Raman Detection of 2,4-Dinitrotoluene Impurity Vapor as a Marker to Locate Landmines," Analytical Chem. 2000, 72, 5834-5840.

Tamao, K., Kawachi, A., "Silyl Anions," Adv. Organomet. Chem., 1995, 38, 1-58.

W. H. Dennis, J., Rosenblatt, D. H., Blucher, W. G., Coon, C. L., "Improved Synthesis of TNT Isomers," J. Chem. Eng. Data 1975, 12, 202-203.

Webber, S. E., "The Role of Time-Dependent Measurements in Elucidating Static Versus Dynamic Quenching Processes," Photochem. and Photobiol 1997, 65, 33-38.

West, R., Sohn, R., Bankwitz, U., Calabrese, J., Apelog, Y., Mueller, T., "Dilithium Derivative of Tetraphenylsilole: An $n^1$-$n^5$ Dilithium Structure" J. Am. Chem. Soc., 1995, 117, 11608-11609.

Xu, Y., Fujino, T., Naito, R., Dolunaru, T., Oka, K., Sohn, H., West, R., "Electroluminescent Properties of a Novel $\delta^*$-$\pi^*$ Conjugated Polymer, Poly [1,1-2(2,3,4,5-tetraphenylsilole)]," Jpn. J. Appl. Phys., 1999, 38, 6915-6918.

Yamaguchi, Y., "Design of Novel $\delta^*$-$\pi^*$ Conjugated Polysilanes," Synthetic Metals, 1996, 82, 149-153.

Yamaguchi, S., Tamao, K., "Theoretical Study of the Electronic Structure of 2,2'-Bisilole in Comparison with 1,1'-Bi-1,3-Cyclopentadiene: $\delta^*$-$\pi^*$ Conjugation and a Low-Lying LUMO as the Origin of the Unusual Optical Properties of 3,3'4,4'-Tetraphenyl-2,2'-Bisilole," Bull. Chem. Soc. Jpn 1996, 69, 2327-2334.

Yamaguchi, S., Jin, R., Tamao, K., "Silicon-Catenated Silole Oligomers: Oligo(1,1-silole)s," Organometallics, 1997, 16, 2486.

Yamaguchi, S., Tamao, K., "Silole-Containing : $\delta$- and $\pi$-Conjugated Compounds," J. Chem. Soc., Dalton Trans., 1998, 3693-3702.

Yamaguchi, S., Endo, T., Uchida, M., Izumizawa, T., Furukawa, K., Tamao, K. "Toward New Materials for Organic Electroluminescent Devices: Synthesis, Structures, and Properties of a Series of 2,5-Diaryl-3,4-Diphenylsiloles," Chem. Eur. J., 2000, 6, 1683-1692.

Yang, J.-S., Swager, T.M., "Fluorescent Porous Polymer Films as TNT Chemosensors: Electronic and Structural Effects," J. Am. Chem. Soc., 1998, 120, 11864-11873.

Yang, J.-S., Swager, T. M., "Porous Shape Persistent Fluorescent Polymer Films: An Approach to TNT Sensory Materials," J. Am. Chem. Soc., 1998, 120, 5321-5322.

Sohn, H., Huddleston, R. R., Powell, D. R., West, R., "An Electroluminescent Ploysilole and Some Dichlorooligosiloles," J. Am. Chem. Soc., 1999, 121, 2935-2936.

* cited by examiner

PHOTOLUMINESCENT POLYMETALLOLES AS CHEMICAL SENSORS

This application claims the benefit of U.S. Provisional Application Ser. No. 60/322,908, filed Sep. 15, 2001, under 35 U.S.C. § 119.

This work is supported by the National Science Foundation (Grant CHE-0111376) and DARPA's Tactical Sensors Program via a Space and Naval Warfare Systems Center Contract (N66001-98-C-8514).

BACKGROUND OF THE INVENTION

1. Field of the Invention

The present invention relates, in general, chemical sensing and, more particularly, to improved chemical sensors providing both selectivity and high sensitivity. Most particularly, the present invention relates to polysole

2. Description of Related Art

Detecting hazardous chemicals in our environment is fundamental to economic development, national security and the quality of life. The ever-increasing demand for better sensing or detection technologies to address needs in many different areas, including but not limited to, such as the detection of concealed explosives in airports, land and water mines, chemical agents that are extremely hazardous at trace levels, or industrial toxic waste produced by chemical plants. To be effective, a chemical sensing technology must provide a high degree of sensitivity, selectivity, stability, robustness and portability. Significant advances in the current chemical sensing technology will be immeasurably beneficial to national and global needs.

Of the many transduction mechanisms existing for chemical sensing, optical absorption, in particular, is widely used. Although the ultimate sensitivity of an optical absorption measurement is limited by quantum noise arising from the discrete nature of light, this limit is rarely achieved in practice.

Chemical sensors for nitroaromatics (NcQuade, D. T.; Pullen, A. E.; Swager, T. M. *Chem. Rev.* 2000, 100, 2537-2574; Albert, K. J.; Lewis, N. S.; Schauer, C. L.; Sotzing, G. A.; Stitzel, S. E.; Vaid, T. P.; Walt, D. R. *Chem. Rev.* 2000, 100, 2595-2626), which offer new approaches to the rapid detection of ultra-trace analytes from explosives, have attracted a great deal of attention in recent years, because explosives are important chemical species to detect in mine fields (Rouhi, A. M. *Chem. Eng. News* 1997, 75, 14-22) military applications, remediation sites, and homeland security applications (Fainberg, A. *Science* 1992, 255, 1531-1537). It is also important in forensic investigations, such as post-blast residue determinations (Barshick, S. A. *J. Forensic Sci.* 1998, 43, 284-293; Smith, K. D.; McCord, B. R.; McCrehan, W. A.; Mount, K; Rowe, W. F. *J. Forensic Sci* 1999, 44, 789-794). Metal detectors, widely used as portable instrumentation for field explosive detection, cannot locate the plastic casing of modern land mines. Trained dogs are expensive, difficult to maintain and are easily tired (Czarnik, A. W. *Nature* 1998, 394, 417-418). Physical detection methods for explosives include gas chromatography coupled with a mass spectrometer (Hakansson, K; Coorey, R. V.; Zubarev, R. A.; Talrose, V. L.; Hakansson, P. *J. Mass Spectrom* 2000, 35, 337-346), surface-enhanced Raman spectroscopy (Sylvia, J. M.; Janni, J. A.; Klein, J. D.; Spencer, K. M. *Anal. Chem.* 2000, 72, 5834-5840), nuclear quadrupole resonance (Anferov, V. P.; Mozjoukhine, G. V.; Fisher, R. *Rev. Sci. Instrum.* 2000, 71, 1656-1659), energy-dispersive X-ray diffraction (Luggar, R. D.; Farquharson, M. J.; Horrocks, J. A.; Lacey, R. J. *J. X-ray Spectrom.* 1998, 27, 87-94), neutron activation analysis, electron capture detection (Rouhi, A. M . *Chem. Eng. News* 1997, 75, 14-22), and cyclic voltammetry (Krausa, M.; Schorb, K. *J. Electroanal. Chem.* 1999, 461, 10-13). These techniques are highly selective, but some are expensive and others not easily fielded in a small, low-power package.

Most detection methods for explosives are only applicable to air samples due to interference problems encountered in complex aqueous media. Sensing TNT and picric acid in groundwater or seawater is important for the detection of buried unexploded ordnance and for locating underwater mines (Shriver-Lake, L. C.; Donner, B. L.; Ligler, F. S. *Environ. Sci. Technol.* 1997, 31, 837-841; Lu, J.; Zhang, Z. *Analytica Chimica Acta* 1996, 318, 175-179). There are also environmental applications for characterizing soil and groundwater contaminated with toxic TNT at military bases and munitions production and distribution facilities (*Approaches for the remediation of federal facility sites contaminated with explosive or radioactive wastes.*; U. S. Environmental Protection Agency: Washington, D.C., 1993). Organic polymers and optical fibers (Albert, K. J.; Myrick, M. L.; Brown, S. B.; James, D. L.; Milanovich, F. P.; Walt, D. R. *Environ. Sci. Technol.* 2001, 35, 3193-3200) have been previously studied to detect vapors of explosive analytes (McQuade, D. T.; Pullen, A. E.; Swager, T. M. *Chem. Rev.* 2000, 100, 2537-2574; Albert, K. J.; Lewis, N. S.; Schauer, C. L; Sotzing, G. A; Stitzel, S. E.; Vaid, T. P.; Walt, D. R. *Chem. Rev.* 2000, 100, 2595-2626). The transduction methods used include absorption, fluorescence, conductivity, etc. Such simple techniques are promising because they can be incorporated into inexpensive and portable microelectronic devices. For example, a chemically selective silicone polymer layer on a SAW (surface acoustic wave) device has been shown to provide efficient detection for the nitroaromatic compounds (McGill, R. A.; Mlsna, T. E.; Mowery, R. In *IEEE International Frequency Control Symposium,* 1998, pp 630-633). Recently, it was reported that the fluorescence of pentiptycene polymers (Yang, J. S.; Swager, T. M. *J. Am. Chem. Soc.* 1998, 120, 5321-5322:; Yang, J. S.; Swager, T. M. *J. Am. Chem. Soc.* 1998, 120, 11864-11873) and polyacetylene (Liu, Y.; Mills, R. C.; Boncella, J. M.; Schanze, K. S. *Langmuir* 2001, 17, 7452-7455) are highly sensitive to nitroaromatic molecules. Previously Inventors communicated that the inorganic polymer, poly (tetraphenyl) silole 1, is an excellent material for the detection of explosives by fluorescence (Sohn, H.; Calhoun, R. M.; Sailor, M. J.; Trogler, W. C. *Angew. Chem. Int. Ed. Engl.* 2001, 40, 2104-2105). The work disclosed herein describes a broad class of easily prepared luminescent inorganic polymeric sensors for nitroaromatic compounds. Detection is based on photoluminescence quenching of polymers containing a metallole ring and Si—Si, Si—Ge, and Ge—Ge backbones.

Especially at this juncture of world history, there is a compelling need for highly sensitive and highly selective explosives detectors. There are approximately 5 mil in Europe, 7.5 mil US and 1 mil in Asia who had their baggage checked in the year 2000. Over $2 billion being spent to currently equip 76 largest US airports with X-ray CAT explosive detection systems. The United States Coast Guard oversees 6 million imported containers. US Customs initiated CSI (container security initiative ) after September 11[th]. It screens 489 million passengers/yr, comprised of 67 million air, 11 million ships, 328 million automobiles and 47 million pedestrians at 301 ports of entry.

US Military and NATO combined deploy more than 30,000 metal detectors as landmine sensors. There are about 100 million landmines, 6 million in Bosnia alone, scattered around world resulting in about 2000 casualties/month.

The US Homeland Security program must deal with protection of, but not limited to, water and air resources, food supplies, nuclear plants, chemical companies, oil refineries, gas storage areas, prisons, embassies, federal buildings, courts, corporate headquarters, banks, tunnels, Olympic venues, railway and subway terminals, underground parking areas, police stations, post offices, mailboxes, schools, lockers and passport scanners. Our waterways must be swept clean of water mines.

Furthermore, basic environmental monitoring is necessary, for example, of ground water at munitions facilities and ranges.

These efforts require astronomic expenditures of taxpayer money. For example, leading companies producing explosives detectors are:

Invision (CAT-ray Scan, unit cost 600K-1.5 mil, 268 units sold in 2001)

Barringer (ion scan, 45-60K),

Graseby Security (ion scan, 45K)

Thermedics (gc/chemiluminescence, 30-170K)

Quantum Magnetics (NQR, 65K)

AS&E (X-ray backscatter, 150K)

Explosive Detection Dogs (dogs, 8.5-25 K)

Moreover, ubiquitous metal detectors such as walk through (4-5K) and wands ($200-400). Dept. of Education advocates purchase 400,000 hand-held units.

In view of the above, it is clear that there is a great need for inexpensive and highly efficient inorganic polymer sensors that can detect nitroaromatic compounds, such as picric acid, nitrobenzene, 2,4-dinitrotoluene (DNT) and 2,4,6-trinitrotoluene (TNT) in air or seawater. An important aspect of the inorganic polymer sensors is their insensitivity to common environmental interferents.

SUMMARY OF THE INVENTION

The primary object of this invention is to provide highly efficient inorganic polymer sensors that can detect nitroaromatic compounds, such as picric acid, nitrobenzene, 2,4-dinitrotoluene (DNT) and 2,4,6-trinitrotoluene (TNT).

Another object in accordance with the present invention is to provide a sensor that is functional in detecting nitroaromatic compounds in air.

Another object of this invention is to provide a sensor capable of detecting hazardous contaminants on solid surfaces.

A further, most preferred object is to provide a sensor capable of detecting concealed hazardous chemicals or explosives.

Another preferred object of this invention is to provide the apparatus to conveniently deploy the abovenamed sensor under varying field conditions.

Another highly preferred object of this invention is to provide methods for making the abovenamed polymer sensors.

A further object according to this invention is to provide highly efficient, highly selective and highly sensitive polymer sensors that are inexpensive so that their benefits may be more universally realized.

In accordance with these objects, this invention contemplates a method for detecting electron deficient molecules in air, water or other surfaces by preparing photoluminescent polymetalloles, placing the prepared polymetalloles into a quartz flow cell containing analytes, subjecting the contents of the flow cell to light and measuring the quenching of photoluminescence of the polymetallole against a standard. The flow cell can be filled with air, water, such as seawater or other liquid.

The contemplated method further involves.

A more specific and preferred embodiment of this invention is a method for detecting concealed explosives. These explosives may be carried in containers, dispersed into air or water. An example is a water mine, shedding explosives residue into seawater. Most preferably, the molecule to be detected is a member of the group consisting essentially of NB, DNT, TNT and picric acid.

A most preferred embodiment in accordance with this invention is a method for constructing photoluminescent polysilole polymers that can be efficiently used as highly sensitive and selective sensors.

An equally preferred embodiment in accordance with this invention is a chemical compound with characteristics suitable for the abovenamed tasks. Such a compound can be selected from a group consisting essentially of polysilole 1, polygermole 2, silole-germole alternating copolymer 3, silole-silane copolymers, $(\text{silole-SiR}^1\text{R}^2)_n$, germole-silane copolymers $(\text{germole-SiR}^1\text{R}^2)_n$.

Still further embodiments and advantages of the invention will become apparent to those skilled in the art upon reading the entire disclosure contained herein.

Tamao, K., Uchida, M., Izumizawa, T., Furukawa, K. & Yamaguchi, S. J. Am. Chem. Soc. 118, 11974-11975 (1996).

Sohn, H., Huddleston, R. R., Powell, D. R. & West, R. J. Am. Chem. Soc. 121, 2935-2936 (1999).

Figure 22:
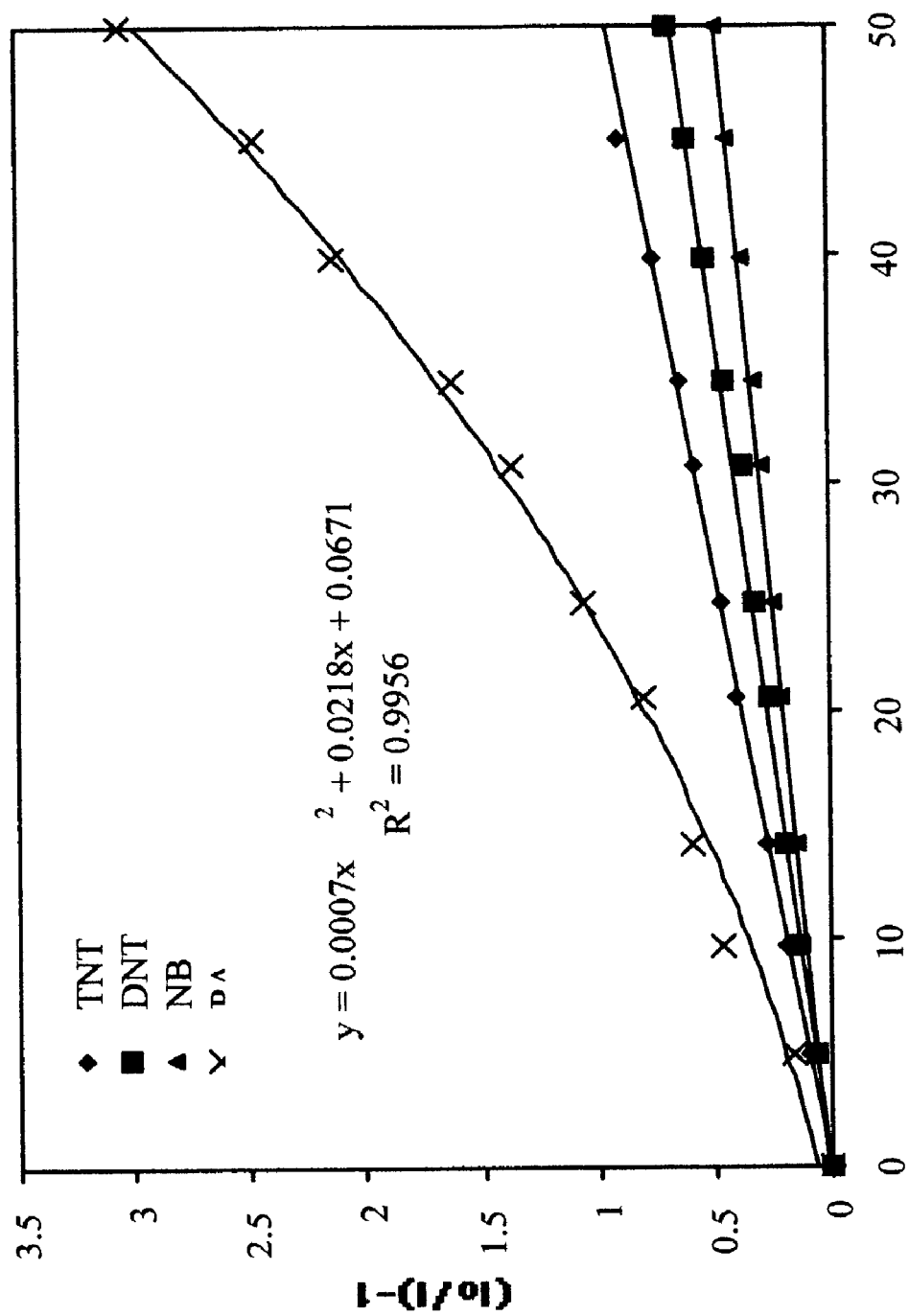

FIG. 22 shows Stern-Volmer Plots of the sensitivity and selectivity of the sensors of this invention in the detection of explosives in toluene: (TNT, DNT, Picric Acid).

Figure 23:
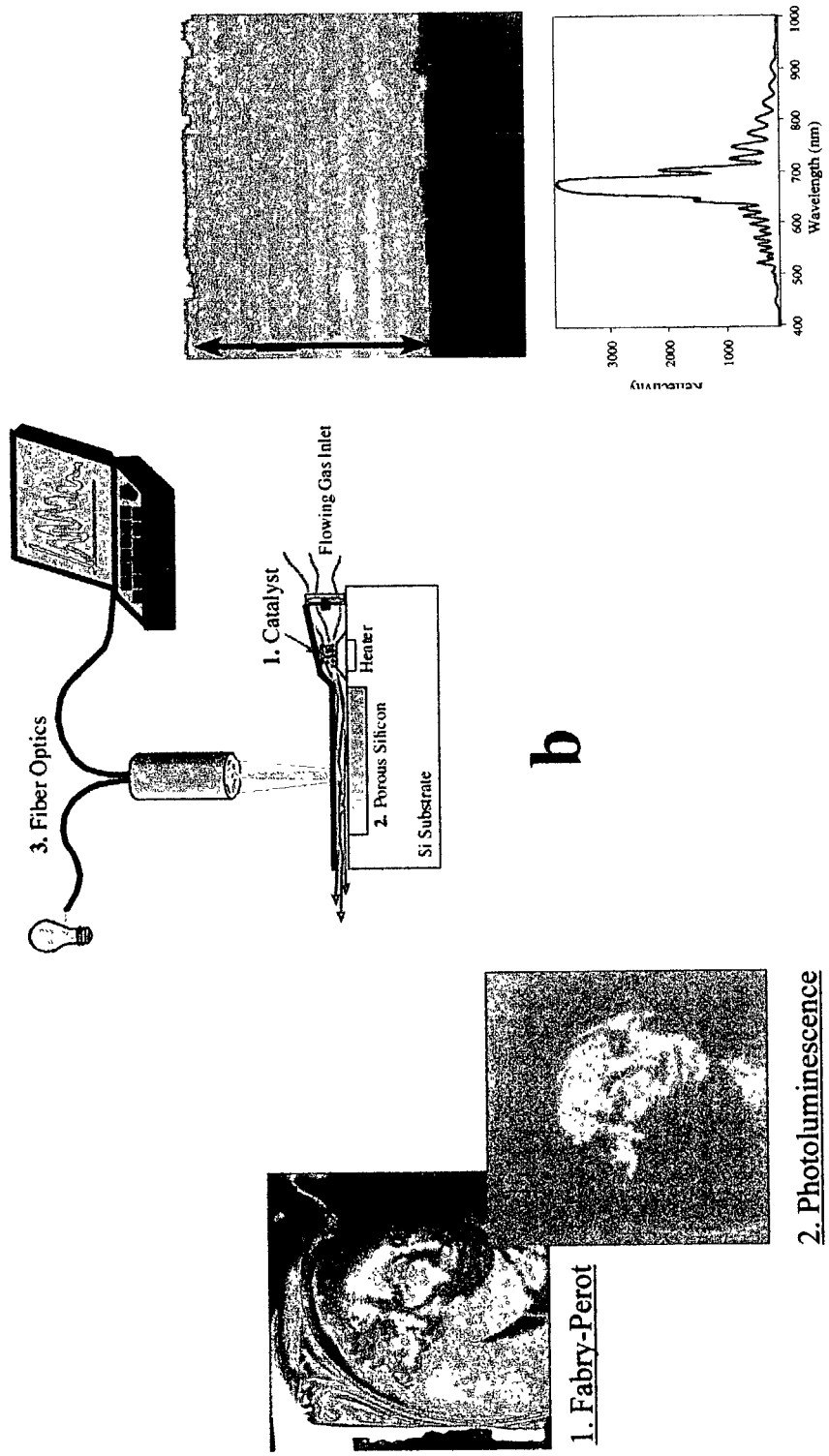

FIG. 23 demonstrates the nanoengineered silicon sensors methodology. a. Luminescence from silicon nanodots and nanowires 1. Fabry-Perot 2. 1photoluminescence. b. Specificity: transducer: a. reflectivity from porous si films. 1. Catalysis, 2. Electronic properties. c. Sensitivity: 1. Photonic crystal materials, 2. Optical nanostructures.

Figure 24:
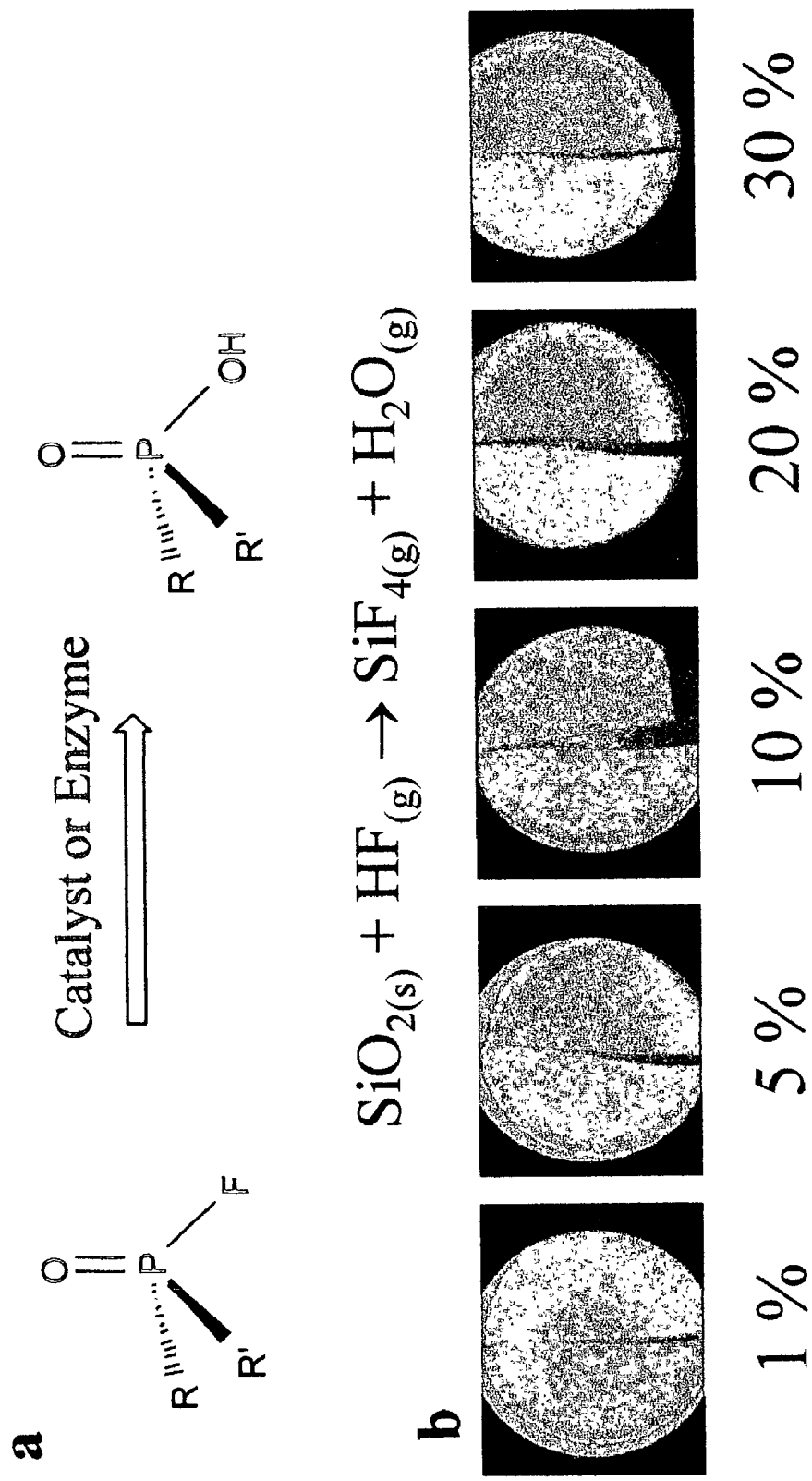

FIG. 24 indicates the specificity of the sensors. a. Catalytic Hydrolysis of CW Agents. b. Right half exposed to vapor over aqueous HF at the indicated concentrations.

Figure 25:
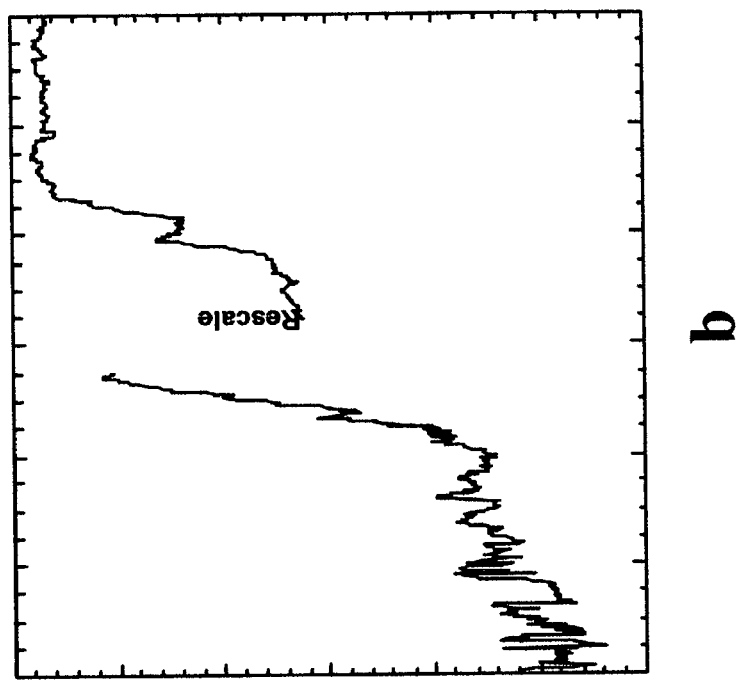
Figure 25:
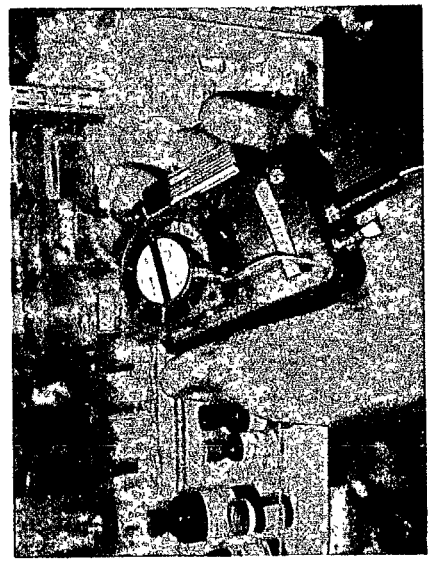

FIG. 25 Laser interferometer using nanocrystalline porous si transducers. a. Dynamic range: 5 decades b. Detection limit (ethanol): 500 ppb.

Handheld nanosensor device for nerve agent developed for DARPA Micro Unattended Ground Sensors program b. Sarin run showing response to Sarin at 10 ppm within 7 min of introduction. The sampling chamber depleted of agent ca. 10 min into the run. (Dr. Kwok Ong, APGEA).

Figure 26:
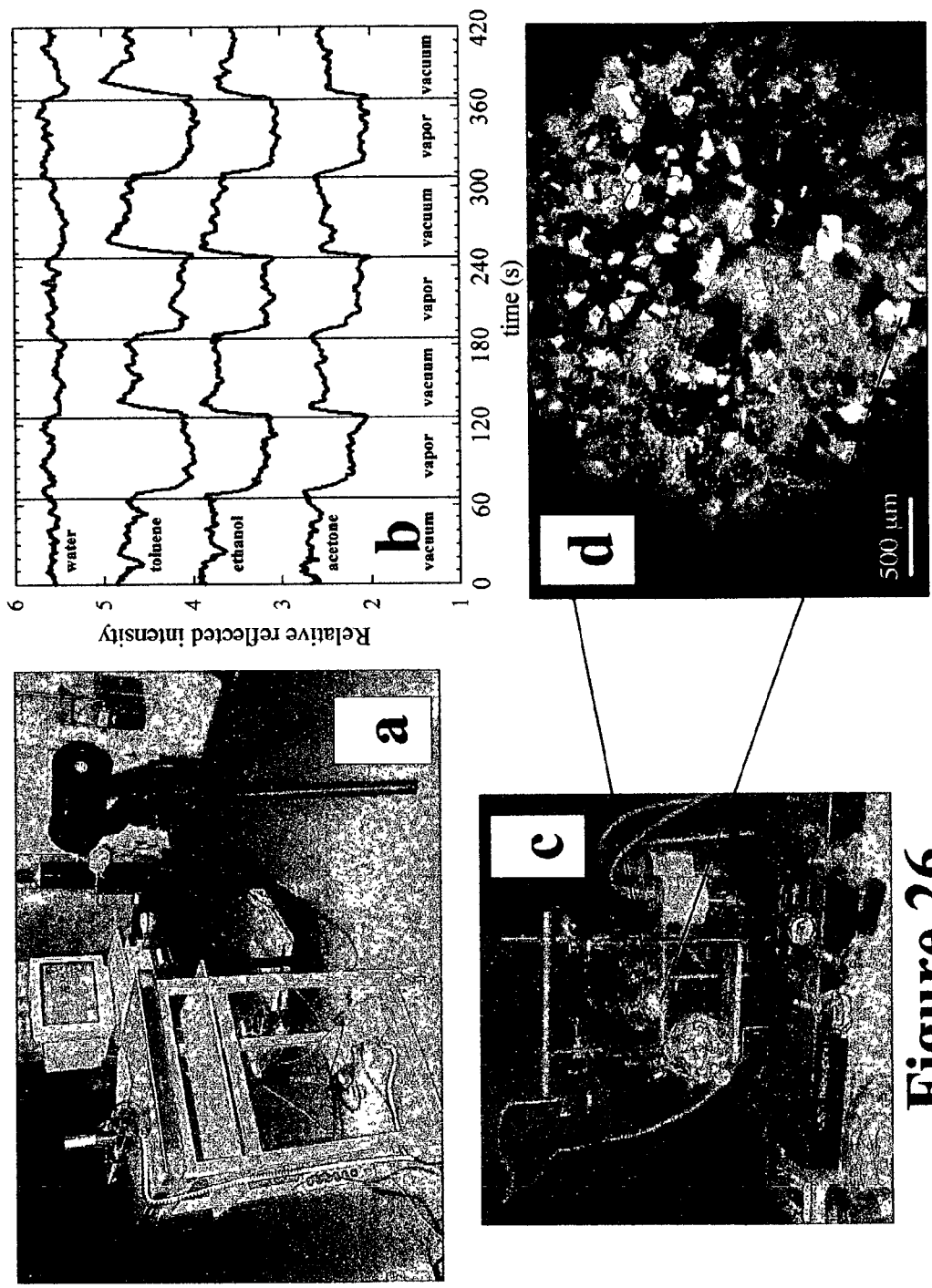

FIG. 26 Standoff Detection of VOCs with nanostructured Si photonic bandgap particles. a.

DESCRIPTION OF THE PREFERRED EMBODIMENTS

Introduction

The work described herein represents development of inexpensive inorganic polymeric sensors that can provide a sensitivity and selectivity for explosive nitroaromatic compounds. Selectivity can be provided by the arrays of 12 different reactive fluorescent sensors to mimic the human olfactory system. The sensors are based on photoluminescence quenching of polymers containing metalloid-metalloid backbones such as Si—Si, Si—Ge or Ge—Ge. The sensor employs a thin film of plhotoluminescent copolymers, which is stable in air, water, acids, common organic solvents and even seawater containing bioorganisms.

Figure 1:
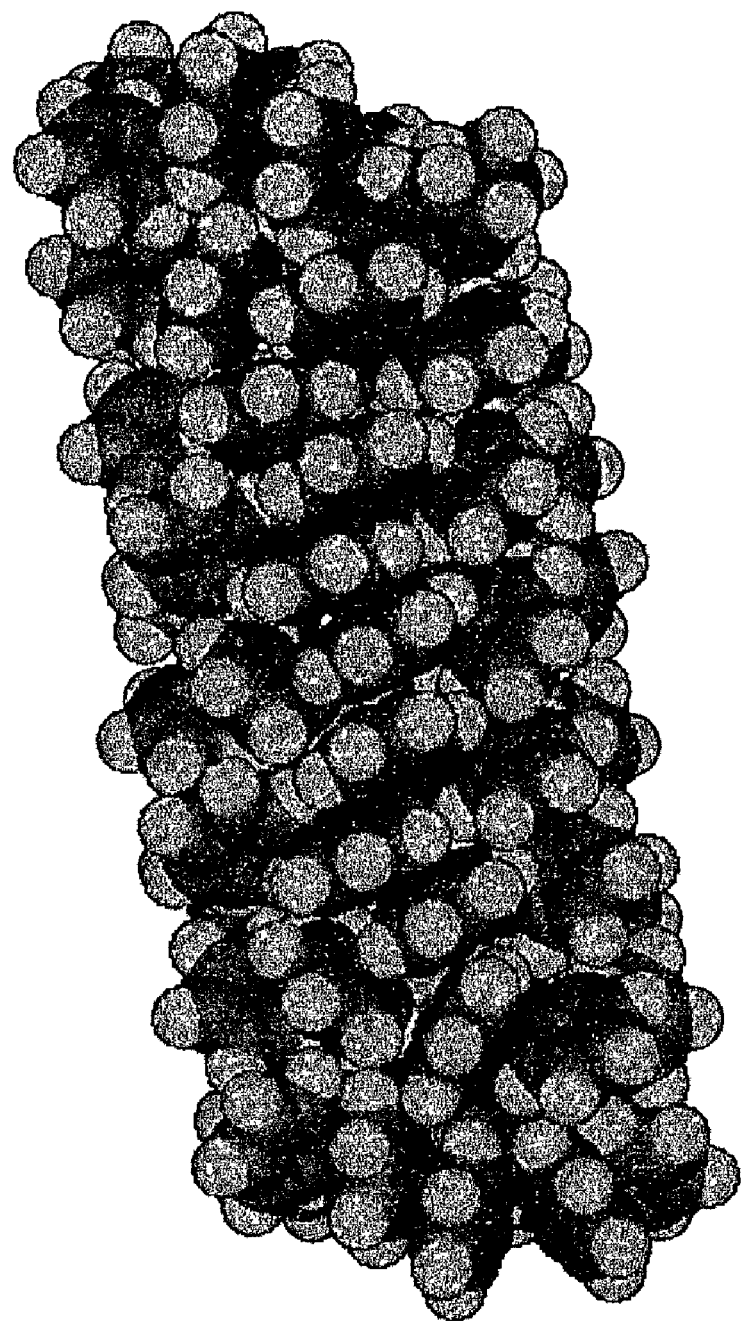
FIG. 1 shows a space-filling model structure of polysilole 1.

Metalloles are silicon or germanium-containing metallacyclopentadienes (Tamao, K.; Kawachi, A. Adv. Organomet. Chem. 1995, 38, 1-58). Since silole and germole dianions $(RC)_4Si^{2-}$ and $(RC)_4Ge^{2-}$, R=Ph and Me, have been studied by X-ray crystallography (West, R.; Sohn, H.; Bankwitz, U.; Calabrese, J.; Apelog, Y.; Mueller, T. J. Am. Chem. Soc. 1995, 117, 11608-11609; West, R.; Sohn, H.; Powell, D. R.; Mueller, T.; Apeloig, Y. Angew. Chem. Int. Ed. Engl. 1996, 35, 1002-1004) and found to be extensively delocalized, metalloles (siloles and germoles) are of considerable current interest (Bankwitz, U.; Sohn, H.; Powell, D. R.; West, R. J. Organomet. Chem. 1995, 499, C7-C9; Freeman, W. P.; Tilley, T. D.; Yap, G. P. A.; Rheingold, A. L. Angew. Chem. Int. Ed. Engl. 1996, 35, 882; Hong, J. H.; Boudjhouk, P.; Castellino, S. Organometallics 1994, 13, 27), both because of their unusual electronic and optical properties (Yamaguchi, S.; Tamao, K. J. Chem. Soc., Dalton Trans. 1998, 3693-3702; Yamaguchi, S.; Endo, T.; Uchida, M.; Izumizawa, T.; Furukawa, K.; Tamao, K. Chem. Eur. J. 2000, 6, 1683-1692) and because of their possible application as electron transporting materials in devices (Tamao, K.; Uchida, M.; Izumizawa, T.; Furukawa, K.; Yamaguchi, S. J. Am. Chem. Soc. 1996, 118, 11974-11975). Polysilanes and polygermanes containing a metal-metal backbone emit in the near UV region, and exhibit high hole mobility, and high nonlinear optical susceptibility, which makes them efficient photoemission candidates for a variety of optoelectronics applications (West, R. In Comprehensive Organometallic Chemistry II; Davies, A. G., Ed.; Pergamon: Oxford, 1995, pp 77-110). These properties arise from σσ delocalization along the M-M backbones and confinement of the conjugated electrons along the backbone. Polymetalloles and metallole-silane copolymers are unique in having both a M-M backbone as well as an unsaturated five-membered ring system. These polymers are highly photoluminescent (Sanji, T.; Sakai, T.; Kabuto, C.; Sakurai, H. J. Am. Chem. Soc. 1998, 120, 4552-4553), and used as light-emitting diodes (LED's) (Sohn, H.; Huddleston, R. R.; Powell, D. R.; West, R. J. Am. Chem. Soc. 1999, 121, 2935-2936; Xu, Y.; Fujino, T.; Naito, H.; Dohmaru, T.; Oka, K.; Sohn, H.; West, R. Jpn. J. Appl. Phys. 1999, 38, 6915-6918) or as chemical sensors (Sohn, H.; Calhoun, R. M.; Sailor, M. J.; Trogler, W. C. Angew. Chem. Int. Ed. Engl. 2001, 40, 2104-2105). Characteristic features of polymetalloles and metallole-silane copolymers include a low reduction potential and a low-lying LUMO due to σπ conjugation arising from the interaction between the σ orbital of silicon or germanium, and the π orbital of the butadiene moiety of the five membered ring (Yamaguchi, Y. Synthetic Met. 1996, 82, 149-153; Yamaguchi, S.; Tamao K. Bull. Chem. Soc. Jpn. 1996, 69, 2327-2334). In addition, the M-M backbones exhibit σσ delocalization, which delocalizes the metallole π electrons along the backbone (West, R. In *Comprehensive Organometallic Chemistry II;* Davies, A. G., Ed.; Pergamon: Oxford, 1995, pp 77-110.). Electron delocalization in these polymers provides a means of amplification, because interaction of an analyte molecule at any position along the polymer chain quenches an excited state or exciton delocalized along the chain. A space filling model structure of 1 is shown in FIG. 1. This structure features a Si—Si backbone inside a conjugated ring system of side chains closely packed on the outside in a helical arrangement. A similar means of amplification is available to quantum-confined semiconductor nanocrystallites, via a three-dimensional silicon network instead of linear silicon wire, where the electron and hole wavefunctions are delocalized throughout the nanocrystal (Content, S.; Trogler, W. C.; Sailor, M. J. *Chem. Eur. J.* 2000, 6, 2205-2213).

Syntheses of polymetalloles and metallole copolymers.

Syntheses of dichloro(tetraphenyl)silole, dichloro(tetraphenyl)germole (West, R.; Sohn, H.; Powell, D. R.; Mueller, T.; Apeloig, Y. *Angew. Chem. Int. Ed. Engl.* 1996, 35, 1002-1004.) and polysilole 1([33]) were reported previously. The synthesis of polygermole 2, shown in equation 1, was analogous to the synthesis of polysilole 1, which is from the Wurtz-type polycondensation. An alternative synthesis of the polysilole and polygermole can be effected by the catalytic dehydrocoupling polycondensation of dihydro(tetraphenyl) silole or dihydro(tetraphenyl)germole with 1 mol % of Wilkinson's catalyst, $Rh(PPh_3)_3Cl$, or $Pd(PPh_3)_4$ (Sohn, H.; Trogler, W. C. manuscript submitted 2002). The latter reactions yield the respective polysilole and polygermole in high yield (ca. 80-90%) and give molecular weights ($M_w$) of 4,000~6,000, similar to those of the Wurtz-type polycondensation (ca. ~30%).

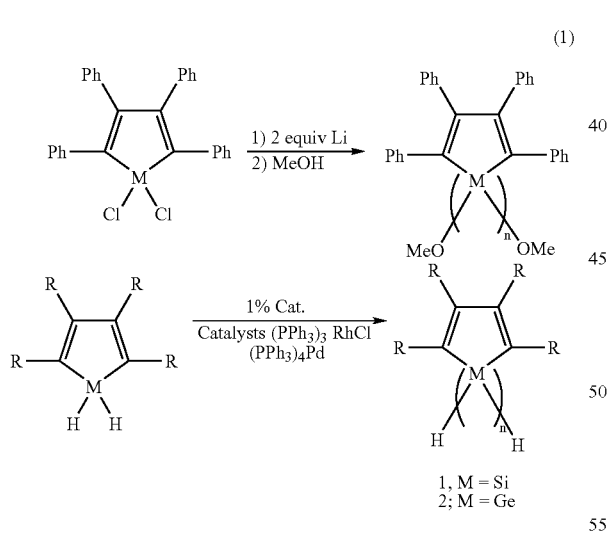

(1)

Silole-germole alternating copolymer 3, in which every other silicon or germanium atom in the polymer chain is also part of a silole or germole ring, was synthesized from the coupling of dichloro(tetraphenyl)germole (West, R.; Sohn, H.; Powell, D. R.; Mueller, T.; Apeloig, Y. *Angew. Chem. Int. Ed. Engl.* 1996, 35, 1002-1004.) and dilithio(tetraphenyl)silole (West, R.; Sohn, H.; Bankwitz, U.; Calabrese, J.; Apelog, Y.; Mueller, T. *J. Am. Chem. Soc.* 1995, 117, 11608-11609.) which is easily obtained from the dichlorotetraphenylsilole by reduction with lithium in about 39% yield. (equation 2) The molecular weight of silole-germole copolymer 3, $M_w$~$5.5\times10^3$, $M_w/M_n$=1.10 determined by SEC (size exclusion chromatography) with polystyrene standards, is similar to that of polysilole or polygermoles. All the polymetalloles are extended oligomers with a degree of polymerization of about 10 to 16, rather than a true high $M_w$ polymer; however, they can be cast into a thin film from solution and show polymer-like properties.

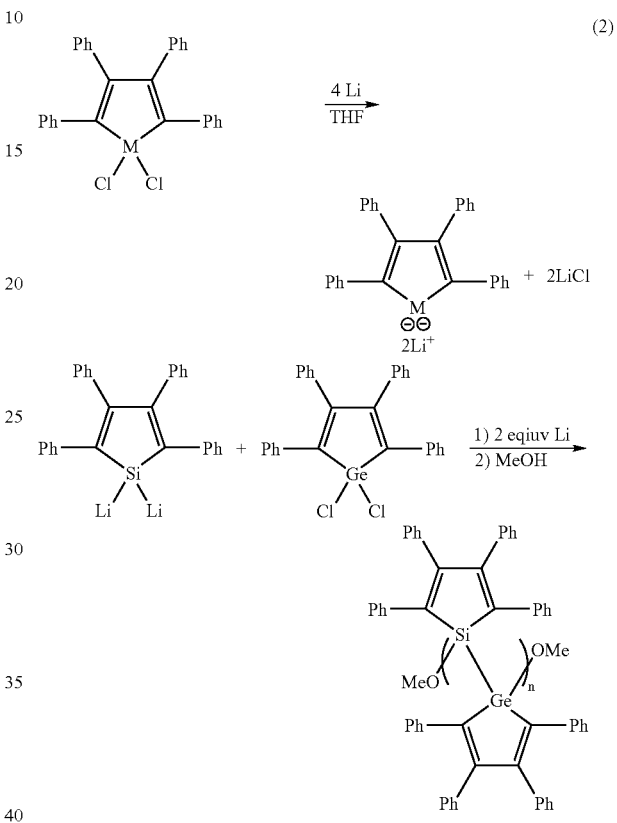

(2)

Silole-silane alternating copolymers 4-8 were also synthesized from coupling of the silole dianion, $(Ph_4C_4Si)Li_2$ (West, R.; Sohn, H.; Bankwitz, U.; Calabrese, J.; Apelog, Y.; Mueller, T. *J. Am. Chem. Soc.* 1995, 17, 11608-11609.) with corresponding silanes. Germole-silane alternating copolymers 9-12 were synthesized from the coupling of germole diaion, $(Ph_4C_4Ge)Li_2$ (West, R.; Sohn, H.; Powell, D. R.; Mueller, T.; Apeloig, Y. *Angew. Chem. Int. Ed. Engl.* 1996, 35, 1002-1004.) with corresponding silanes (equation 3). These reactions generally employ reflux conditions in tetrahydrofuran under an argon atmosphere for 72 h. Some silole-silane copolymers have been previously synthesized by the West and Sakurai groups (Sanji, T.; Sakai, T.; Kabuto, C.; Sakurai, H. *J. Am. Chem. Soc.* 1998, 120, 4552-4553; Sohn, H.; West, R. unpublished studies) and shown to be electroluminescent. We have developed routes to metallole-silane copolymers, which have a hydrosilane between every silole unit, so these copolymers could be easily fuctionalized along the backbone by hydrosilation. The molecular weight of metallole-silane copolymers, $M_n$=$4.1\times10^3$~$5.4\times10^3$, $M_w/M_n$=1.04~1.16 determined by SEC, is similar to that of the polymetalloles. The yields of metallole-silane copolymers are also very similar to those of the Wurtz-type polycondensation (ca. ~35%).

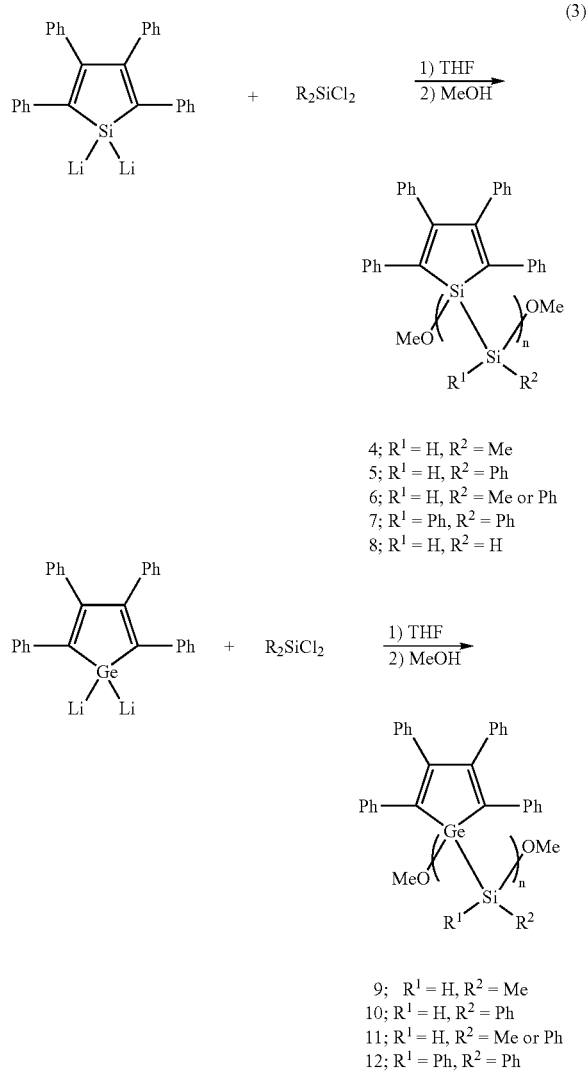

The molecular weights and polydispersity indices (PDI) of polymers 1-12 determined by GPC (gel permeation chromatography) are listed in Table 1. These polymers are soluble in organic solvents, such as tetrahydrofuran, diethlyl ether, toluene, and chloroform.

Absorption and Fluorescence Studies

Figure 2:
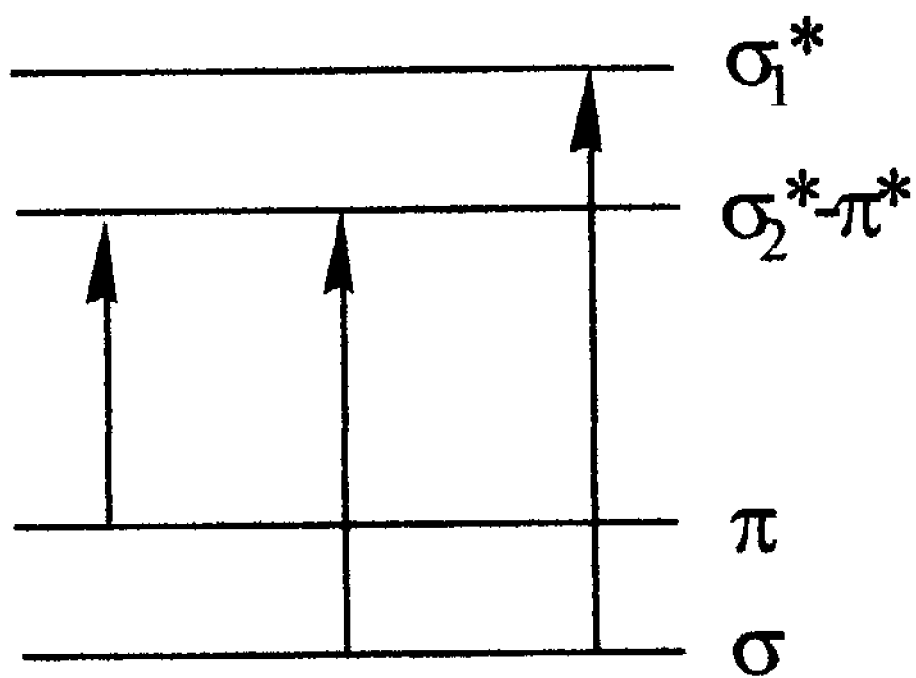
FIG. 2 is a schematic energy-level diagram for polymetalloles and metallole-silane copolymers.
Figure 3:
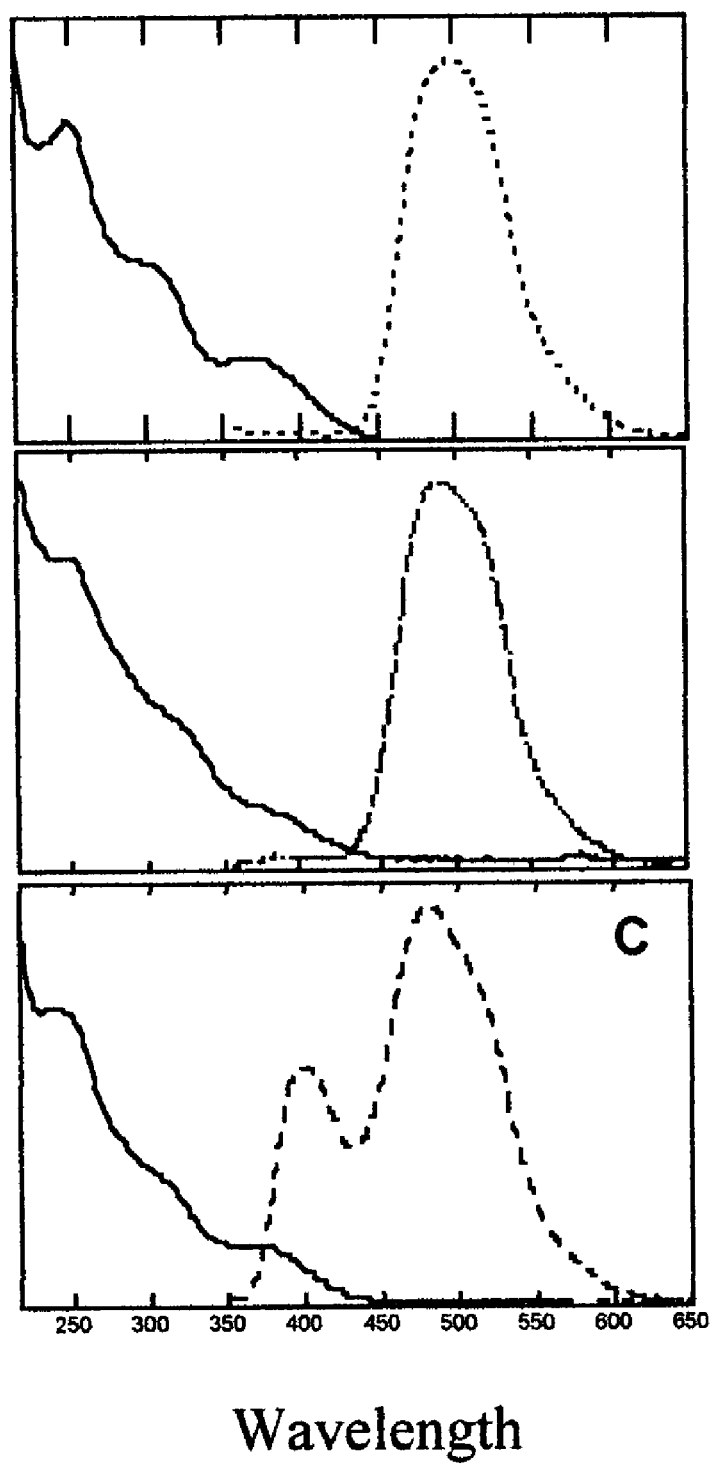
FIG. 3 shows UV-vis absorption spectra in THF (solid line) and fluorescence spectra in toluene (dotted line) for (A) poly (tetraphenyl) germole 2, (B) silole-sitane copolymer 4 and (C) germole-silane copolymer 9.
Figure 4:
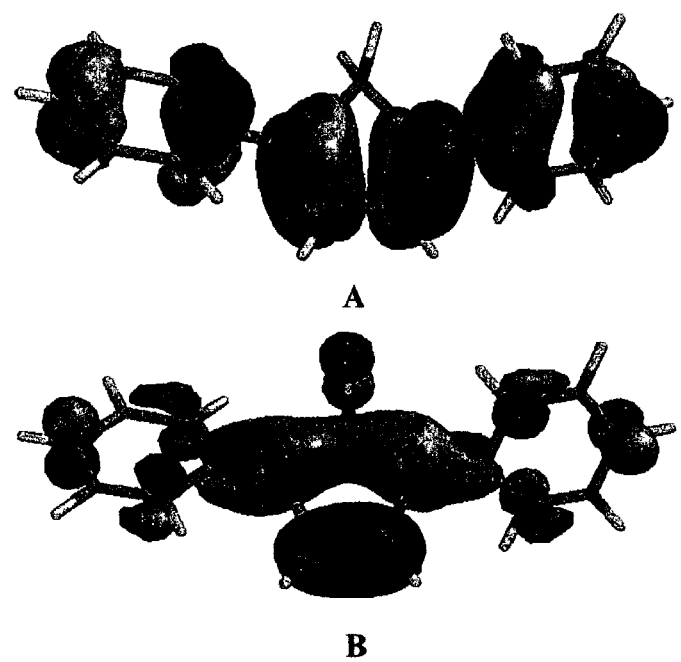
FIG. 4 is a model of HOMO (A) and LUMO (B) of 2,5-diphenylsilole, $\text{Ph}_2\text{C}_4\text{SiH}_2$ from the ab initio calculations at the HF/6-31G* level.
Figure 5:
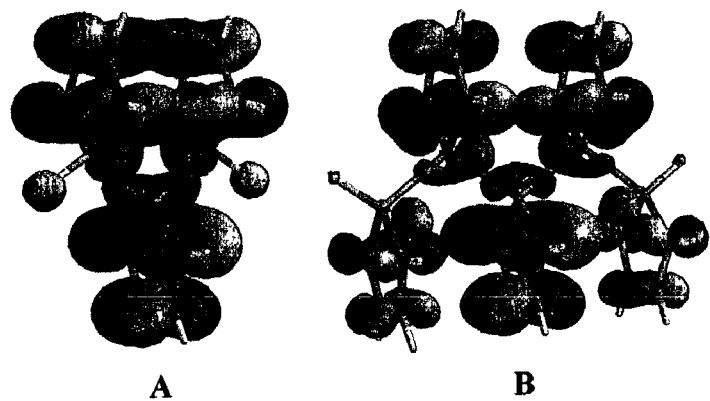
FIG. 5 is a model of LUMO of tersilole (A) and pentasilole (B) from the ab initio calculations at the HF/6-31G* level.

The UV-vis absorption and fluorescence spectral data for the polymers 1-12 are reported in Table 1. The poly(tetraphenylmetallole)s 1-3 and tetraphenylmetallole-silane copolymers 4-12 exhibit three absorption bands which are ascribed to the □–□* transition in the butadiene moiety and □–□$_2$*+□* and □–□$_1$* transitions in the M-M backbones (Xu, Y.; Fujino, T.; Naito, H.; Dohmaru, T.; Oka, K.; Sohn, H.; West, R. *Jpn. J. Appl. Phys.* 1999, 38, 6915-6918.). FIG. 2 shows schematic energy-level diagrams for polymetalloles and metallole-silane copolymers. UV-vis absorption spectra in THF (solid line) and fluorescence spectra in toluene (dotted line) for (A) poly(tetraphenylgermole) 2, (B) silole-silane copolymer 4, and (C) germole-silane copolymer 9 are shown in FIG. 3. Absorptions at the wavelength of about 370 nm for the poly(tetraphenylmetallole)s 1-3 and tetraphenylmetallole-silane copolymers 4-12 are ascribed to the □–□* transition in the butadiene moiety, which are about 89 to 95 nm red-shifted compare to that of oligo[1,1-(2,3,4,5-tetramethylsilole)] (□$_{max}$=275 nm) (Kanno, K; Ichinohe, M.; Kabuto, C.; Kira, M. *Chem. Lett.* 1998, 99) and are about 75 to 81 nm red-shifted compare to that of oligo[1,1-(2,5-dimethyl-3,4-diphenylsilole)] (□$_{max}$=289 nm) (Yamaguchi, S.; Jin, R.; Tamao, K. *Organometallics* 1997, 16, 2486). These red shifts are attributed to the increasing main chain length and the partial conjugation of phenyl groups to the silole ring. FIG. 4 shows the HOMO (A) and LUMO (B) of 2,5-diphenylsilole, Ph$_2$C$_4$SiH$_2$, from the ab initio calculations at the HF/6-31G* level. Phenyl groups at the 2,5 positions involve □-conjugation with the butadiene moiety and the silicon orbital delocalization involves the LUMO. Second absorptions at wavelengths of 304 to 320 nm for the poly(tetraphenylmetallole)s 2-3 and tetraphenylmetallole-silane copolymers 4-12 are assigned to the □–□$_2$*+□* transition, which parallels to that of the polytetraphenylsilole 1. FIG. 5 shows the LUMO of tersilole (A) and pentasilole (B) from the ab initio calculations at the HF/6-31G* level, indicating the □–□$_2$*+□* conjugations primarily involve the LUMO.

Figure 6:
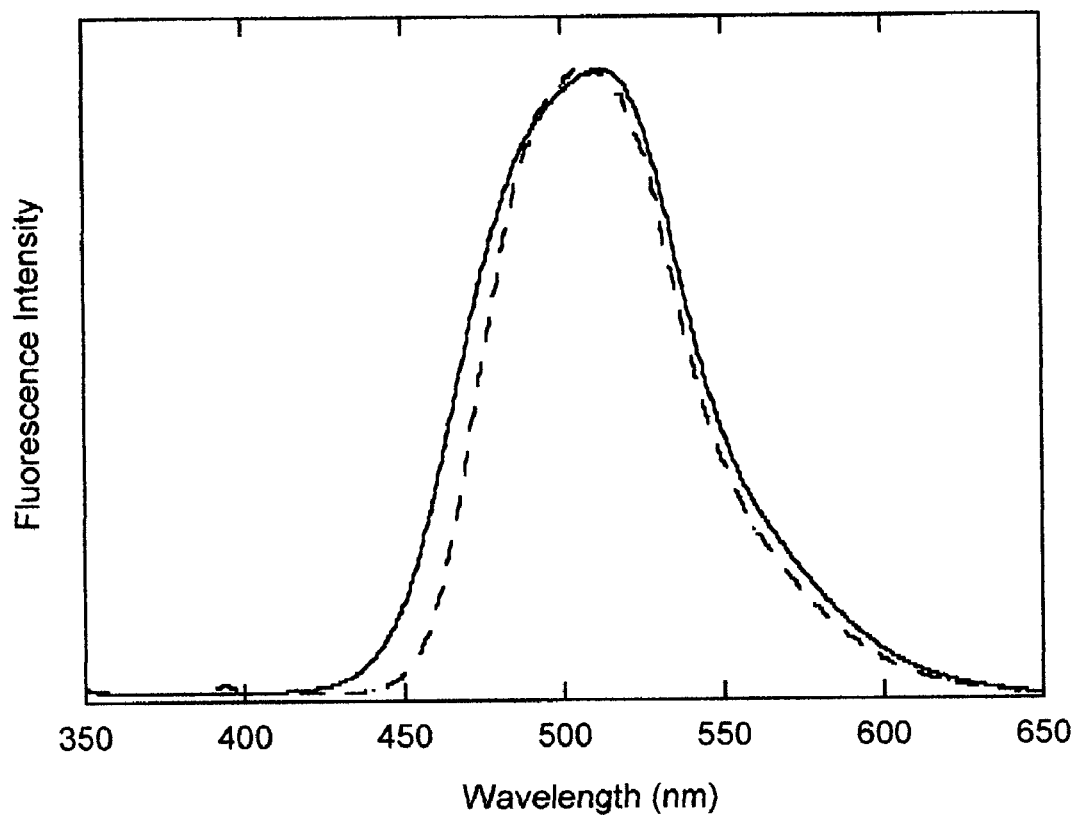
FIG. 6 demonstrates the fluorescence spectra of polysilole 1 in toluene solution (solid line) and in thin solid film (dotted line).

Polymetallole 1-2 and silole-silane copolymers 4-7 exhibit one emission band (□$_{max}$ 486 to 513 nm) with an excitation wavelength of 340 nm, whereas others exhibit two emission bands with □$_{max}$ of 480-510 nm and 385-402 nm. The ratios of the two emission intensities are not concentration dependent, which indicates that an excimer is not the origin. Emission bands for germole-silane copolymers 9-12 are only 2 to 33 nm blue-shifted compared to the other polymers. FIG. 6 shows fluorescence spectra of the poly(tetraphenyl)silole in toluene solution (solid line) and in the solid state (dotted line). The bandwidth of the emission spectrum in solution is slightly larger than in the solid state. There is no shift in the maximum of the emission wavelength. This suggests that the polysilole exhibits neither □—stacking of polymer chains nor excimer formation.

Fluorescence Quenching Studies with Nitroaromatic Analytes

Figure 7:
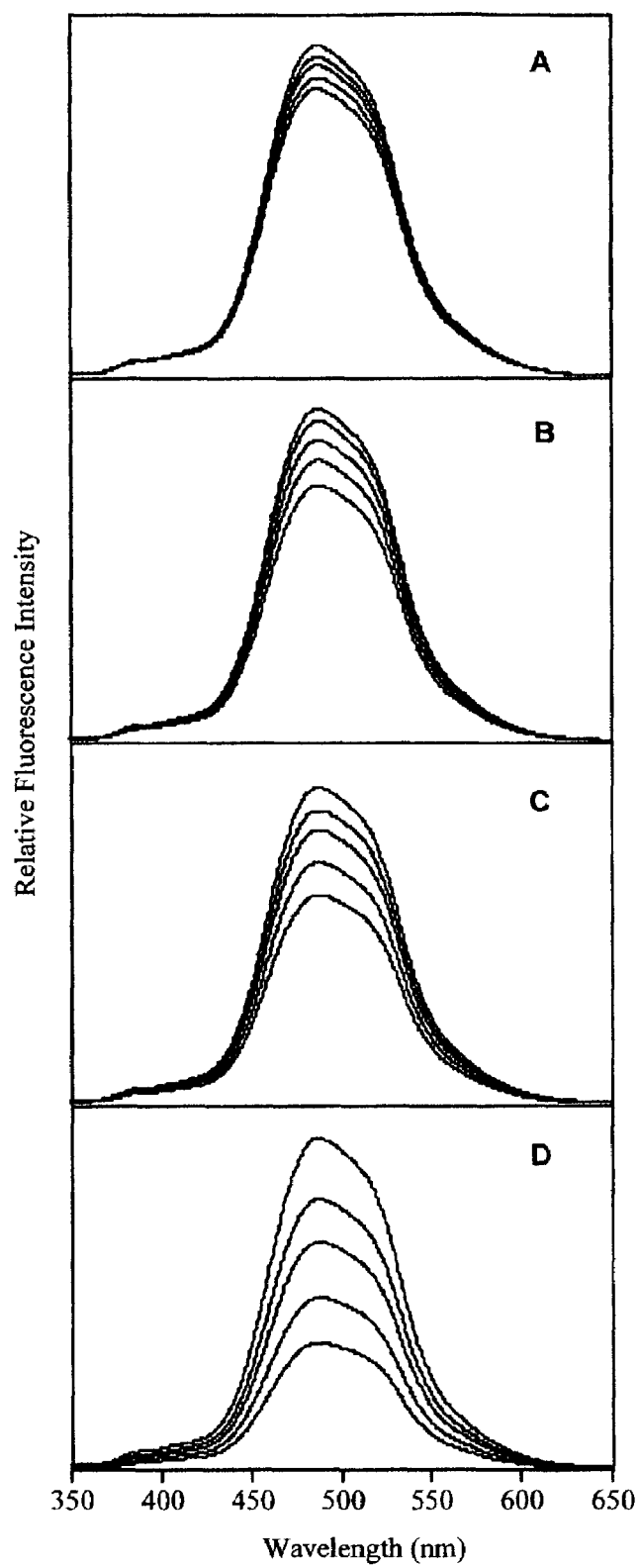
FIG. 7 shows quenching of photoluminescence spectra of silole-silane copolymer 5 with (A) nitrobenzene, from top $2.0\times10^{-5}$ M, $3.9\times10^{-5}$ M, $7.8\times10^{-5}$ M, and $11.5\times10^{-5}$ M, (B) DNT, from top $1.4\times10^{-5}$ M, $3.9\times10^{-5}$ M, $7.8\times10^{-5}$ M, and $12.4\times10^{-5}$ M, (C) TNT, from top $2.1\times10^{-5}$ M, $4.2\times10^{-5}$ M, $8.1\times10^{-5}$ M, and $12.6\times10^{-5}$ M, (D) picric acid, from top $2.1\times10^{-5}$ M, $4.2\times10^{-5}$ M, $8.0\times10^{-5}$ M, and $12.6\times10^{-5}$ M.

The detection method involves measurement of the quenching of photoluminescence of the polymetalloles 1-3 and metallole-silane copolymers 4-12 by the analyte (using a Perkin-Elmer LS 50B fluorescence spectrometer, 340 nm excitation wavelength). Fluorescence spectra of a toluene solution of the polymers 1-12 were obtained upon successive addition of aliquots of picric acid (purchased from Aldrich and recrystallized from ethanol solution before use), TNT (prepared from DNT (W. H. Dennis, J.; Rosenblatt, D. H.; Blucher, W. G.; Coon, C. L. *J. Chem. Eng. Data* 1975, 120, 202-203) and recrystallized twice from the methanol), DNT, and nitrobenzene. Photoluminescence quenching of the polymers 1-12 in toluene solutions with picric acid. TNT, DNT, and nitrobenzene were measured. FIG. 7 displays the quenching photoluminescence spectra of the silole-silane copolymer 5 with (A) nitrobenzene, (B) DNT, (C) TNT, and (D) picric acid. Photoluminescence quenching efficiencies of the polymetalloles 1-3 and metallole-silane copolymers 4-12 are all in order of picric acid>TNT>DNT>nitrobenzene.

The purity of the TNT sample was found to be important to obtain reproducible results. It was synthesized by nitration of dinitrotoluene and recrystallized twice from methanol. A third recrystallization produces the same results as the twice-recrystallized material. When the quenching experiment was undertaken without recrystallization of TNT, higher (ca. 10×) quenching percentages are obtained. Presumably, impurities with higher quenching efficiencies are present in crude TNT.

The Stern-Volmer equation was used to quantify the differences of analytes (Turro, N. J. *Modern Molecular Photo-*

*chemistry;* University Science Books: Sausalito, Calif., 1991). In this equation, $I_o$ is the initial fluorescence intensity without analyte concerned, I is the fluorescence intensity with added analyte, [A] is the concentration of analyte, and Ksv is the Stern-Volmer constant.

$$(I_o/I)-1=Ksv[A]$$

Figure 8:
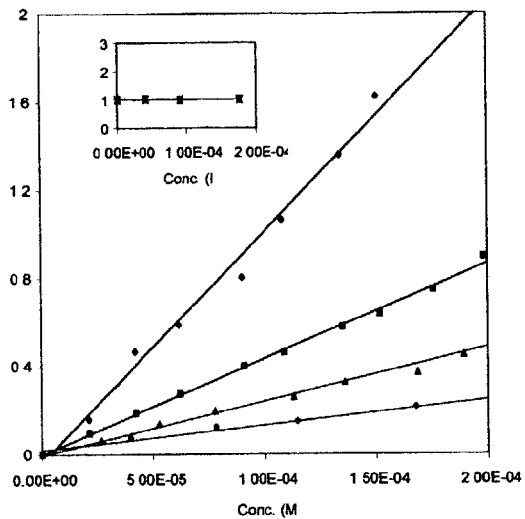
FIG. 8 consists of Stern-Volmer plots; from top polysilole 1, polygermole 2, and silote-silane copolymer 8; (picric acid), (TNT), (DNT), (nitrobenzene); the plots of fluorescence lifetime ($\square_0/\square$), shown as inset, are independent of added TNT.
Figure 8:
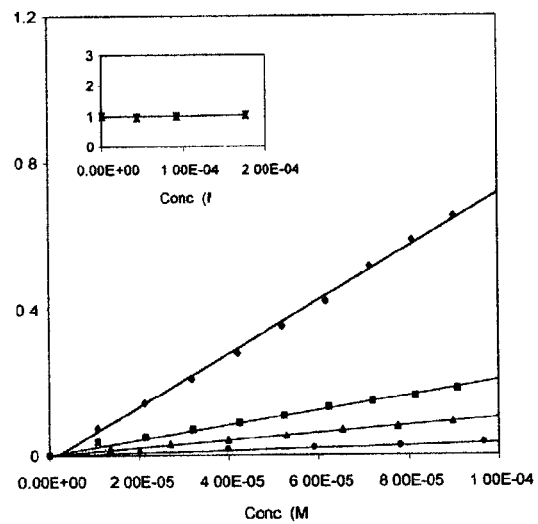
Figure 8:
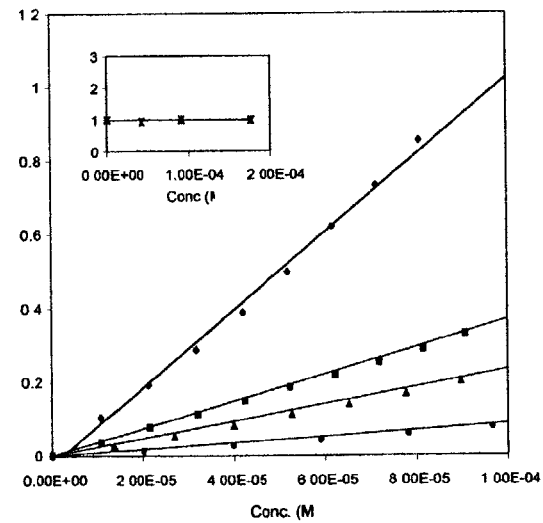

FIG. 8 shows the Stern-Volmer plots of polysilole 1, polygermole 2, and silole-silane copolymer 8 for each analyte. A linear Stern-Volmer relationship is observed in all cases, but the Stern-Volmer plot for picric acid exhibits an exponential dependence when its concentration is higher than $1.0 \times 10^{-4}$ M. A linear Stern-Volmer relationship may be observed if either static or dynamic quenching process is dominant. Thus, in the case of higher concentrations of picric acid, two processes are competitive, which exhibit a nonlinear Stern-Volmer relationship.

Photoluminescence may arise from either a static process, by the quenching of a bound complex, or a dynamic process, by collisionally quenching the excited state (Connors, K. A. *Binding Constants: The Measurement of Molecular Complex Stability;* Wiley-Interscience: New York, 1987; Lakowicz, J. R. *Principles of Fluorescence Spectroscopy;* Plenum Press: New York, 1986). For the foymer case, Ksv is an association constant due to the analyte-preassociated receptor sites. Thus, the collision rate of the analyte is not involved in static quenching and the fluorescence lifetime is invariant with the concentration of analyte. With dynamic quenching, the fluorescence lifetime should diminish as quencher is added.

A single "mean" characteristic lifetime (□) for polymetalloles and metallole-silane copolymers 1-12 has been measured and summarized in Table 1. Luminescence decay was highly heterogeneous in all cases. Three lifetimes were needed to provide an acceptable fit over the first few nanoseconds. Amplitudes of the three components varied but were comparable, none was a negligible feature (and the solvent blank made no contribution). The three lifetimes distributed themselves uniformly (in a geometric sense) over whatever time scale encompassed the total range. These features suggest that the complete description of the fluorescence is actually a continuous distribution of decay rates from a heterogeneous collection of chromophore sites. Since the oligomers span a size distribution, this behavior was not surprising. No special significance should be given to the particular amplitudes and decay times; they simply reproduce the measured curve. Experience suggests that three components are always enough to fit a range of 600 data points for realistic signal-to-noise ratios). The mean lifetime is an average of the three lifetimes determined by the fitting procedure, weighted by their relative amplitudes. This is the appropriate average for comparison with quantum yields, that is, the "amount" of light emitted by different samples under different conditions, such as quenching, as has been treated in the literature (Sillen, A.; Engelboroughs, Y. *Photochem. and Photobiol.* 1998, 67, 475-486). Given this heterogeneity, we were concerned about possible long-lived luminescence that might be particularly vulnerable to quenching. However, measurements with a separate nanosecond laser system confirmed that there were no longer-lived processes than those captured by the time-correlated photon counting measurement and incorporated into Table 1.

TABLE 1

| polymers | $M_w$ | PDI | $\lambda_{abs}$ $\pi-\pi^*$, $\sigma-\sigma_2^*+\pi^*$ (nm) | $\lambda_{fluo}$ (nm) | Ksv (M$^{-1}$) PA | Ksv (M$^{-1}$) TNT | Ksv (M$^{-1}$) DNT | Ksv (M$^{-1}$) NB | $\tau$ ($\times 10^{-9}$ s) |
|---|---|---|---|---|---|---|---|---|---|
| 1 | $6.2 \times 10^3$ | 1.14 | 368, 314 | 513 | 11,000 | 4,340 | 2,420 | 1,200 | 0.70[c] |
| 2 | $4.6 \times 10^3$ | 1.05 | 368, 302 | 499 | 6,710 | 2,050 | 1,010 | 320 | 0.28[d] |
| 3 | $5.5 \times 10^3$ | 1.10 | 364, 302 | 510, 385 | 8,910 | 3,050 | 1,730 | 753 | 0.43 |
| 4 | $4.4 \times 10^3$ | 1.04 | 370, 318 | 491 | 9,120 | 3,520 | 2,060 | 1,150 | 2.33 |
| 5 | $4.5 \times 10^3$ | 1.09 | 370, 320 | 488 | 10,700 | 3,940 | 2,380 | 1,230 | 1.34 |
| 6 | $4.8 \times 10^3$ | 1.16 | 368, 320 | 489 | 8,420 | 3,030 | 2,010 | 735 | 2.20 |
| 7 | $5.0 \times 10^3$ | 1.05 | 368, 318 | 493 | 10,800 | 3,430 | 2,330 | 965 | 0.62 |
| 8 | $4.6 \times 10^3$ | 1.14 | 366, 324 | 505, 385 | 9,350 | 3,680 | 2,340 | 864 | 2.70 |
| 9 | $4.9 \times 10^3$ | 1.12 | 364, 304 | 483, 400 | 10,300 | 3,990 | 2,570 | 1,140 | 0.27 |
| 10 | $4.4 \times 10^3$ | 1.06 | 364, 304 | 486, 400 | 9,990 | 3,330 | 2,000 | 965 | 0.35 |
| 11 | $4.1 \times 10^3$ | 1.06 | 364, 304 | 484, 400 | 8,740 | 3,430 | 2,210 | 986 | 0.26 |
| 12 | $5.4 \times 10^3$ | 1.09 | 364, 306 | 480, 402 | 9,840 | 3,340 | 2,150 | 936 | 0.22 |

Summary of Molecular Weight, Photophysical Data,[a] Stern-Volmer Quenching Constants with Picric Acid, TNT, DNT, and Nitrobenzene Analytes, and Mean Life Times of Emission[b] for Polymers 1-12.
[a]Absorption and fluorescence spectra were taken at the concentration of 2 mg/L in THF and 10 mg/L in toluene, respectively.
[b]Repeatability is about 5% but not less than ±0.04 nanoseconds.
[c]1.77 ns (solid state).
[d]1.17 ns (solid state)

Figure 9:
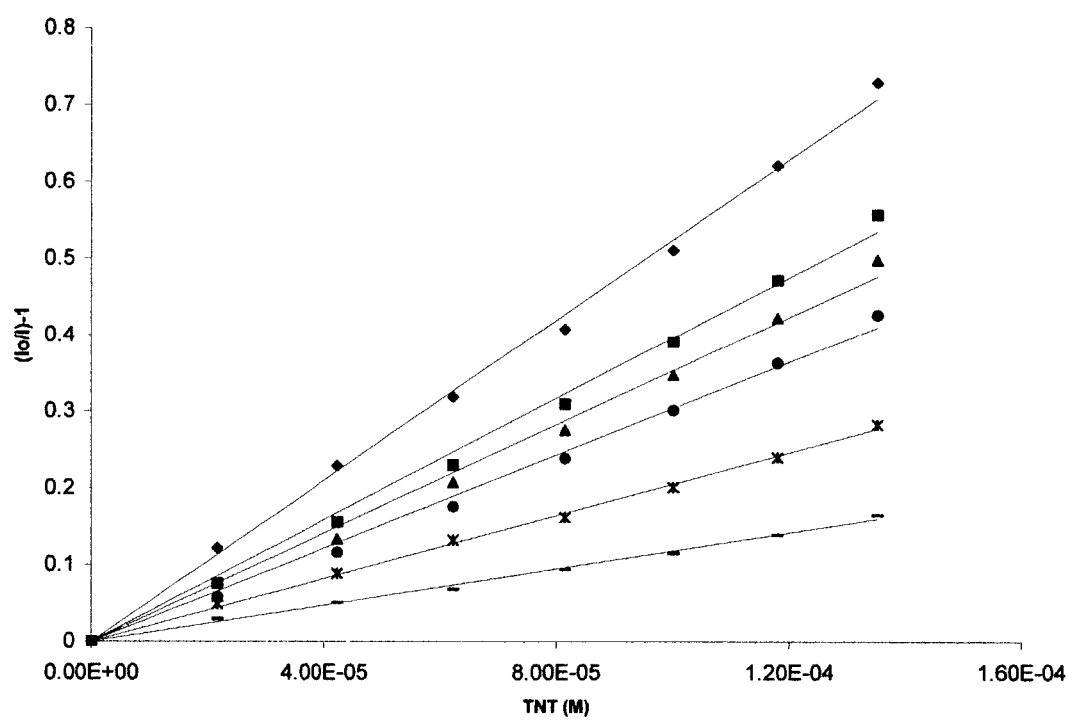
FIG. 9 demonstrates fluorescence decays of polysilole 1 for different concentrations of TNT: 0 M, $4.24\times10^{-5}$ M, $9.09\times10^{-5}$ M, $1.82\times10^{-4}$ M.

It is notable that polysilole 1 and silole-silane copolymers 4-8 have about 3 to 11 times longer fluorescence lifetimes than polygeimole 2 and germole-silane copolymers 9-12. Fluorescence lifetimes in the thin films (solid state) for polysilole 1 and polygermole 2 are 2.5 and 4.2 times longer than in toluene solution respectively. The fluorescence lifetimes as a function of TNT concentration have been also measured and shown in the inset of FIG. 8 for 1, 2 and 8. No change of lifetime has been observed by adding TNT, indicating that the static quenching process is dominant for polymetalloles and metallole-silane copolymers 1-12 (FIG. 9). Some issues with such analyses have been discussed in the literature (Webber, S. E. *Photochem. and Photobiol.* 1997. 65, 33-38). This result suggests that the metallole might act as a receptor and a TNT molecule would intercalate between metallole moieties. The chemical equation for static quenching is as follows, where P-Q is assumed to be completely quenched, when one molecule of analyte intercalates. This probably is over simplified given the dependence of Ksv on analyte redox potential.

Figure 10:
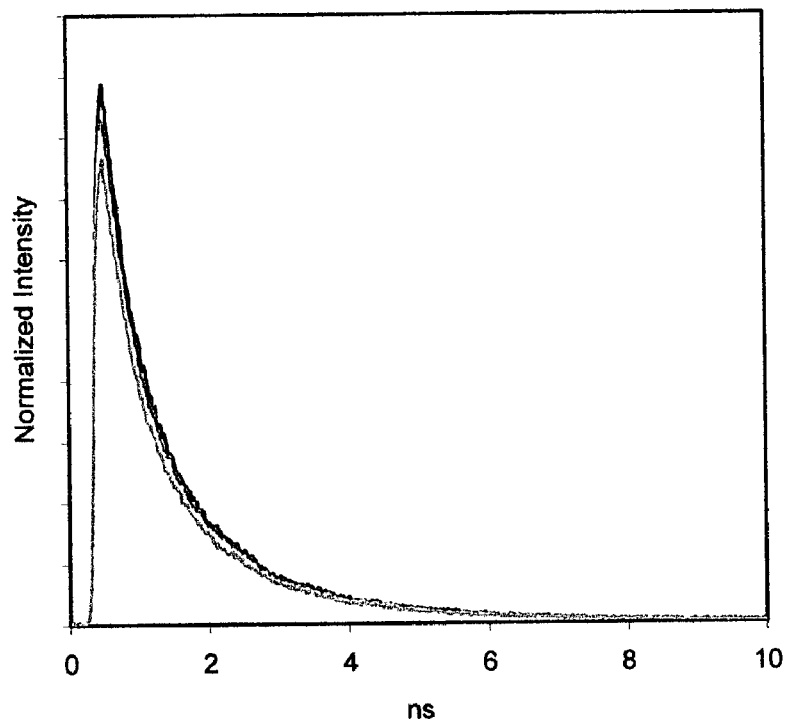
FIG. 10 Stern-Volmer plots of polymers; (polymer 1), (polymer 5), (polymer 4), (polymer 6), (polymer 2), and—(organic pentiptycene-derived polymer 13), for TNT.

For chemosensor applications it is useful to have sensors with varied responses. Each of the 12 polymers exhibit a different ratio of the photoluminescence quenching for picric acid, TNT, DNT, and nitrobenzene and a different response with the same analyte. The use of sensor arrays is inspired by the performance of the olfactory system to specify an analyte (Albert, K. J.; Lewis, N. S.; Schauer, C. L.; Sotzing, G. A.; Stitzel, S. E.; Vaid, T. P.; Walt, D. R. Chem. Rev. 2000, 100, 2595-2626.). FIG. 10 displays the Stern-Volmer plots of polymers 1, 2, 4, 5, and 6 for TNT, indicating that the range of photoluminescence quenching efficiency for TNT is between $2.05 \times 10^3$ and $4.34 \times 10^3$ $M^{-1}$. The relative efficiencies of photoluminescence quenching of poly(tetraphenylmetallole)s 1-3 and tetraphenylmetallole-silane copolymers 4-12 were obtained for picric acid, TNT, DNT, and nitrobenzene, as indicated by the values of Ksv determined from the slopes of the steady-state Stern-Volmer plots and summarized in Table 1. We have also synthesized polymer 13, an organic pentiptycene-derived polymer (Yang, J.-S.; Swager, T. M. J. Am. Chem. Soc. 1998, 120, 5321-5322.; Yang, J.-S.; Swager, T. M. J. Am. Chem. Soc. 1998, 120, 11864-11873.) The metallole copolymers are more sensitive to TNT than the organic pentiptycene-derived polymers for comparison. For example, polysilole 1 ($4.34 \times 10^3$ $M^{-1}$) has about a 371% better quenching efficiency with TNT than organic pentiptycene-derived polymer ($1.17 \times 10^3$ $M^{-1}$).

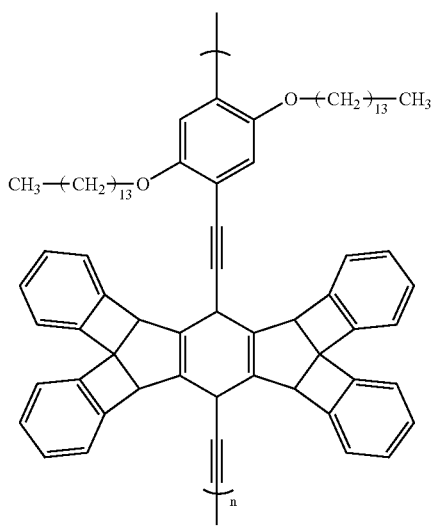

13

Figure 11:
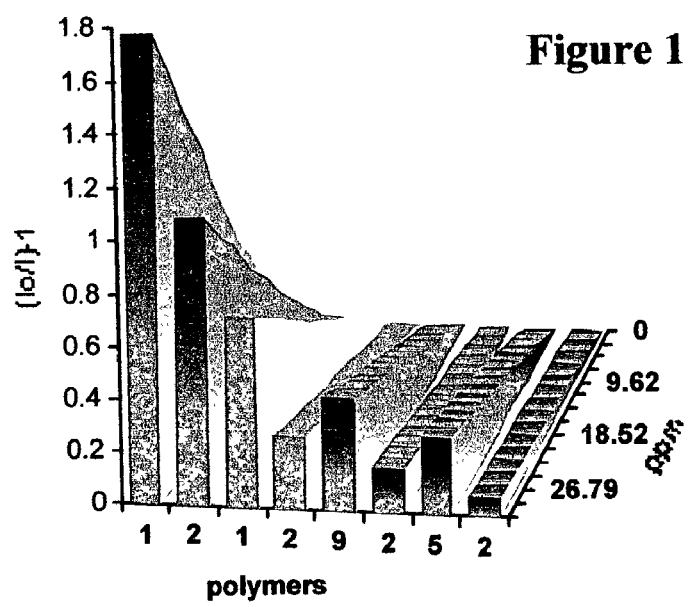
FIG. 11. Highest and lowest photoluminescence quenching efficiency for picric acid, TNT, DNT and nitrobenzene.
Figure 12:
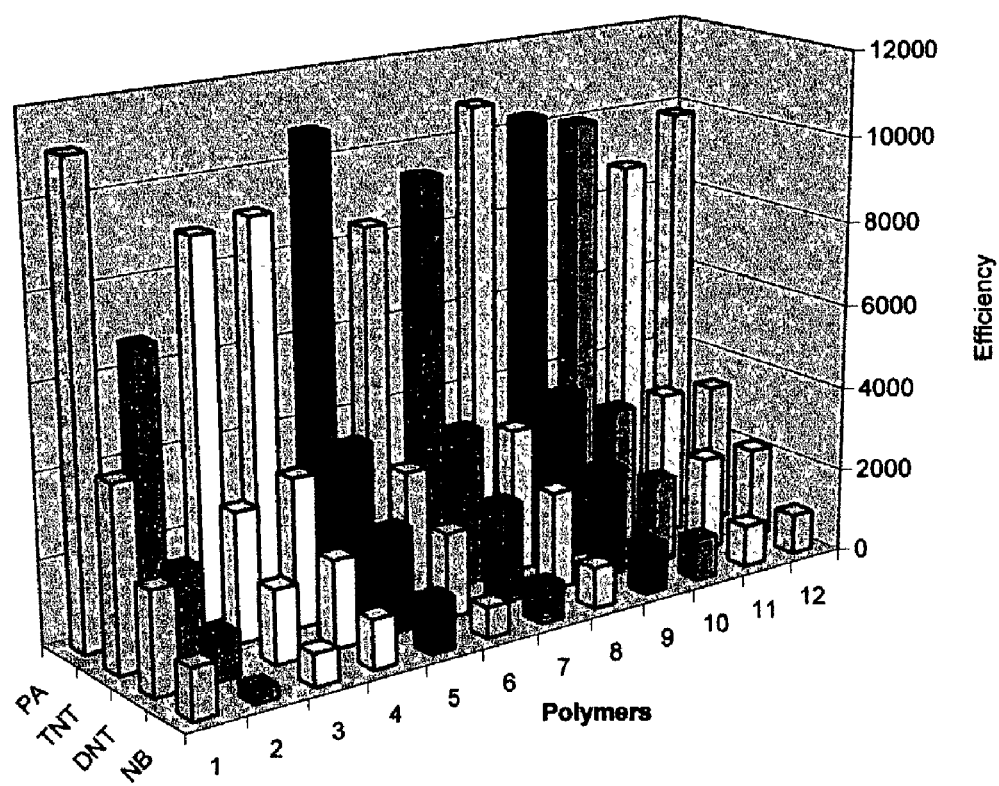
FIG. 12. Array of multi-sensors as a photoluminescence quenching.

The trend in Stern-Volmer constants usually reflects an enhanced charge transfer interaction from metallole polymer to analyte. For example, the relative efficiency of photoluminescence quenching of polysilole 1 is about 9.2:3.6:2.0:1.0 for picric acid, TNT, DNT, and nitrobenzene, respectively. While polysilole 1 shows best photoluminescence quenching efficiency for picric acid and TNT, polymer 9 and 5 exhibit best quenching efficiency for DNT and nitrobenzene, respectively (FIG. 11). Polygermole 2 has the lowest quenching efficiency for all analytes. Since the polymers 1-12 have a similar molecular weight, the range of quenching efficiencies with the same analyte would be expected to be small. Polysilole 1 ($11.02 \times 10^3$ $M^{-1}$ and $4.34 \times 10^3$ $M^{-1}$) exhibits 164 and 212% better quenching efficiency than polygermole 2 ($6.71 \times 10^3$ $M^{-1}$ and $2.05 \times 10^3$ $M^{-1}$) with picric acid and TNT, respectively. Polymer 9 ($2.57 \times 10^3$ $M^{-1}$) has 253% better quenching efficiency than polymer 2 ($1.01 \times 10^3$ $M^{-1}$) with DNT. Polymer 5 ($1.23 \times 10^3$ $M^{-1}$) has 385% better quenching efficiency than metallole polymer 2 ($0.32 \times 10^3$ $M^{-1}$) with nitrobenzene. FIG. 12 illustrates how an analyte might be specified using an array of multi-sensors.

Figure 13:
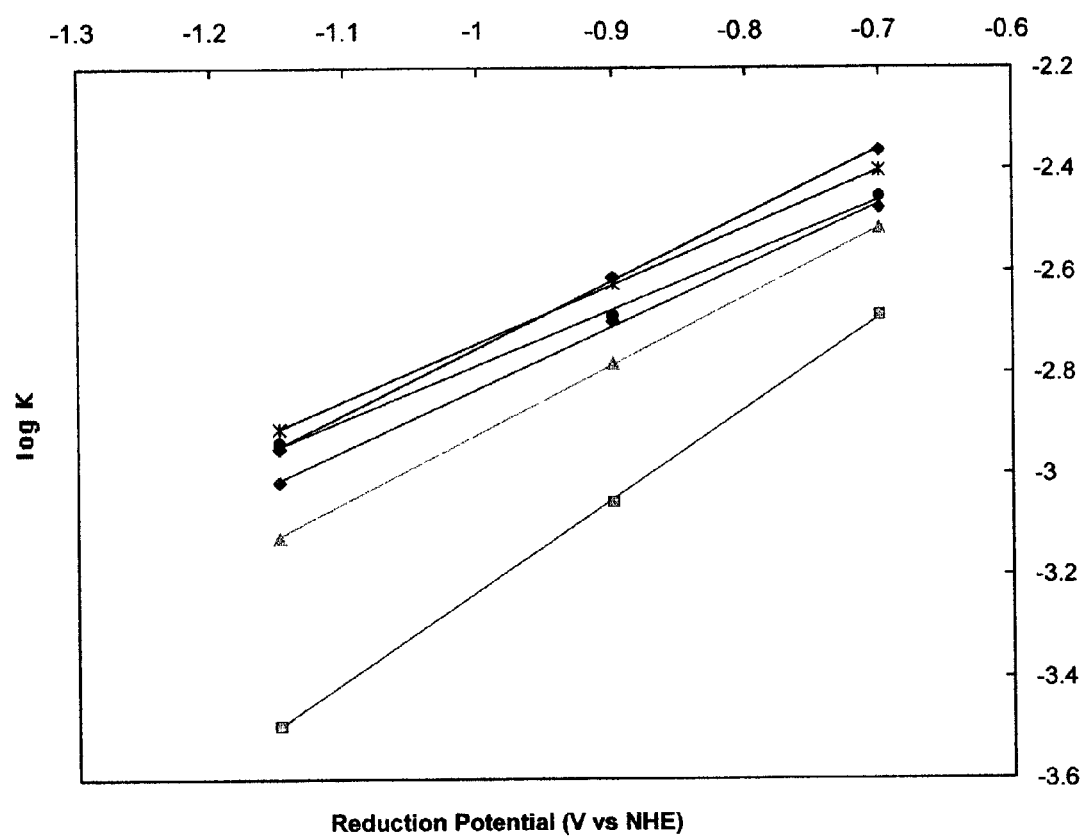
FIG. 13. Plot of log K vs reduction potential of analytes; (polymer 1), (polymer 2), (polymer 3), (polymer 4), (polymer 5), and—(polymer 10).
Figure 14:
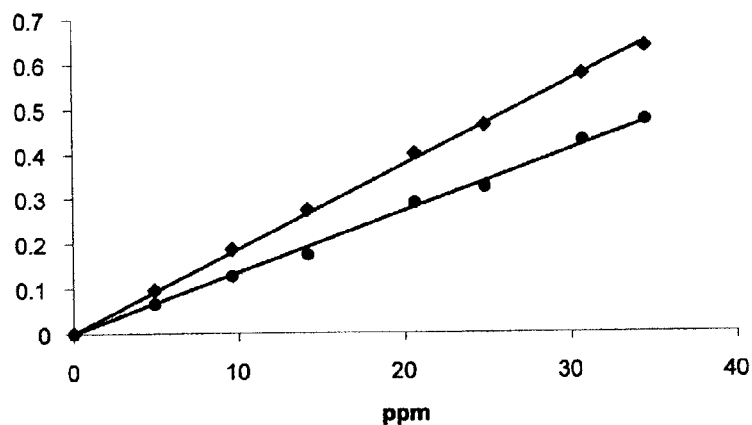
FIG. 14. Schematic diagram of electron transfer mechanism for quenching the photoluminescence of polymetallole by analyte.

FIG. 13 shows a plot of log Ksv vs reduction potential of analytes. All metallole polymers exhibit a linear relationship, even though they have different ratios of photoluminescence quenching efficiency to analytes. This result indicates that the mechanism of photoluminescence quenching is primarily attributable to electron transfer from the excited metallole polymers to the LUMO of the analyte. Since the reduction potential of TNT (-0.7 V vs. NHE) (Yang, J.-S.; Swager, T. M. J. Am. Chem. Soc. 1998, 120, 11864-11873.) is less negative than that of either DNT (-0.9 V vs. NHE) or nitrobenzene (-1.15 V vs. NHE), it is detected with high sensitivity. A schematic diagram of the electron transfer mechanism for the quenching of photoluminescence of the metallole polymers with analyte is shown in FIG. 14. Optical excitation produces an electron-hole pair, which is delocalized through the metallole copolymers. When an electron deficient molecule, such as TNT is present, an electron transfer quenching occurs from the conduction band of the metallole copolymers to the LUMO of the analyte.

Figure 15:
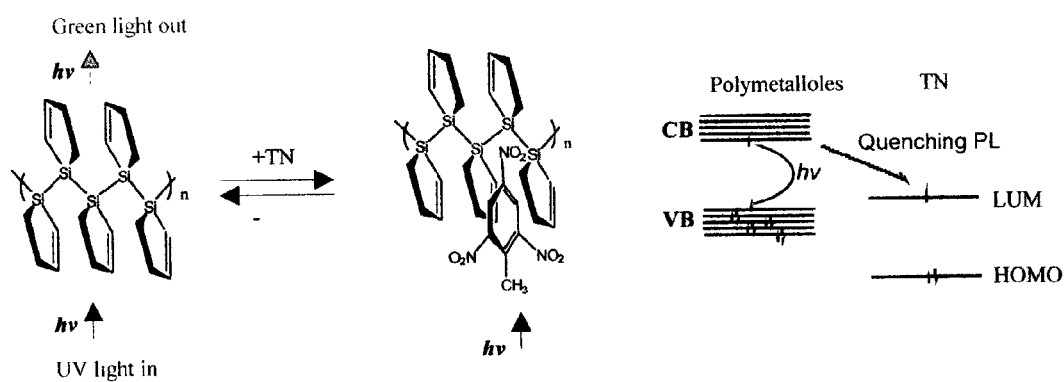
FIG. 15. Stern-Volmer plots of the oligomeric tersilole ( ) vs. polysilole 1 ( ).

To evaluate the efficiency of photoluminescence quenching depending on the chain length of the molecule, we measured the photoluminescence quenching of the oligomeric tersilole, $Cl(C_4Ph_4Si)_3Cl$, (Sohn, H.; Huddleston, R. R.; Powell, D. R.; West, R. J. Am. Chem. Soc. 1999, 121, 2935-2936.) by TNT. FIG. 15 compares the photoluminescence quenching between tersilole and polysilole 1, which has about 16 repeat units. The Ksv value of $4.34 \times 10^3$ $M^{-1}$ for polysilole, is 38 greater than that for the oligomer tersilole (Ksv=$3.14 \times 10^3$ $M^{-1}$). (Sohn, H.; Calhoun, R. M.; Sailor, M. J.; Trogler, W. C. Angew. Chem. Int. Ed. Engl. 2001, 40, 2104-2105. ) This result suggests that the polysilole produces an excited state that is delocalized over many repeat units. For organic polymers, the sensitivity of the photoluminescence quenching technique depends both on the polymer molecular weight and on the diffusion length of excitation (Zhou, Q.; Swager, T. M. J. Am. Chem. Soc. 1995, 117, 7017-7018).

Figure 16:
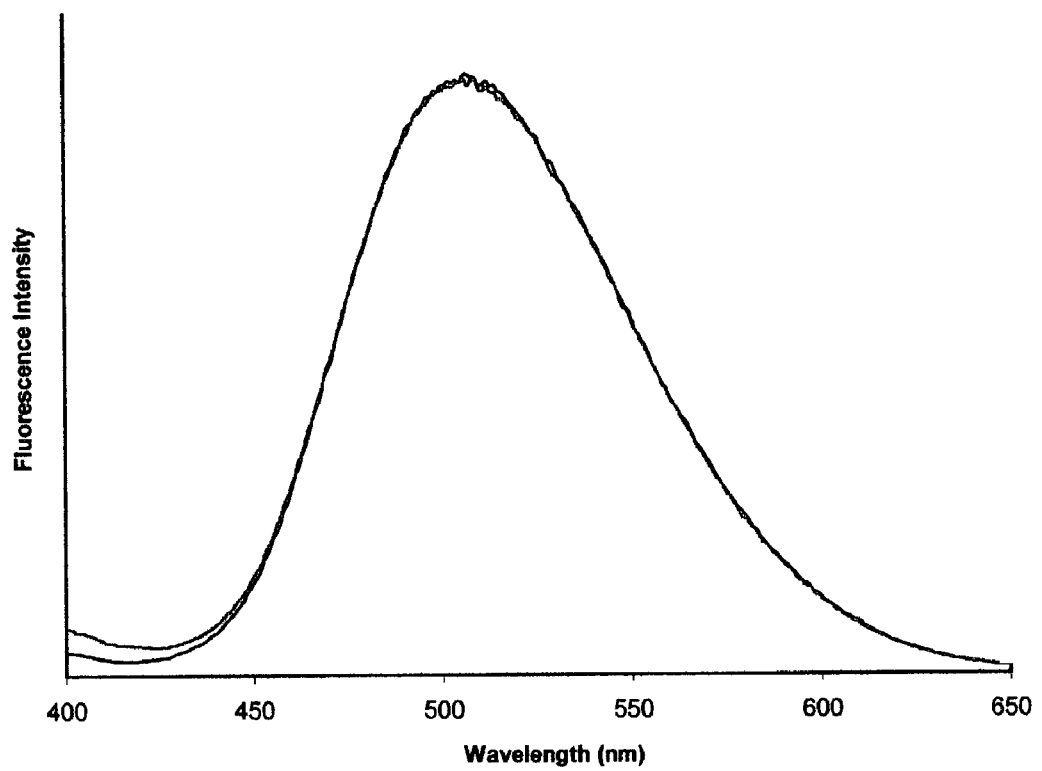
FIG. 16. Quenching of photoluminescence spectra of polysilole 1 with 4 parts per hundred of THF.

An important aspect of the metallole copolymers is their insensitivity to common interferents. Control experiments using both solutions and thin films of metallole copolymers (deposited on glass substrates) with oxygenated air displayed no change in the photoluminescence spectrum. Similarly, exposure of metallole copolymers as a both solution and thin films to organic solvents such as toluene, THF, and methanol or the aqueous inorganic acids $H_2SO_4$ and HF produced no significant decrease in photoluminescence intensity. FIG. 16 shows that the photoluminescence spectra of polysilole 1 in toluene solution display no quenching of fluorescence with 4 parts per hundred of THF. While the organic pentiptycene-derived polymer 13 with the organic oxidant benzoquinone (Ksv=998 $M^{-1}$) exhibits higher quenching efficiency of photoluminescence compared to that of polysilole 1 (Ksv=674 $M^{-1}$), the ratio of quenching efficiency of polysilole 1 with TNT vs. benzoquinone is much greater than that of polymer 13. The Ksv value of $4.34 \times 10^3$ $M^{-1}$ of polysilole 1 for TNT is 644% greater than that for benzoquinone (Ksv=674 $M^{-1}$), but the organic polymer 13 exhibits slightly better quenching efficiency for TNT (Ksv=$1.17 \times 10^3$ $M^{-1}$) (ca. 117%) compared to that for benzoquinone. This result indicates that polysilole 1 exhibits less response to interferences and greater response to nitroaromatic compounds compared to the pentiptycene-derived polymer 13.

Experimental Section

EXAMPLE 1

General. All synthetic manipulations were carried out under an atmosphere of dry argon gas using standard vacuumline Schlenk techniques. All solvents were degassed and purified before use according to standard literature methods: diethyl ether, hexanes, tetrahydrofuran, and toluene were purchased from Aldrich Chemical Co. Inc. and distilled from sodiunm/benzophenone ketal. Spectroscopic grade toluene from Fisher Scientific was used for the fluorescence measurements. NMR grade deuteriochloroform was stored over 4 Å molecular sieves. All other reagents (Aldrich, Gelest) were used as received or distilled before use. NMR data were collected with Varian Unity 300, 400, or 500 MHz spectrometers (300.1 MHz for $^1$H NMR, 75.5 MHz for $^{13}$C NMR and 99.2 MHz for $^{29}$Si NMR). Chemical shifts are reported in parts per million (□ ppm); downfield shifts are reported as positive values from tetramethylsilane (TMS) standard at 0.00 ppm. The $^1$H and $^{13}$C chemical shifts were referenced relative to CHCl$_3$(□=77.0 ppm) as an internal standard, and the $^{29}$Si chemical shifts were referenced to an external TMS standard. Samples dissolved in CDCl$_3$, unless otherwise stated. $^{13}$C NMR were recorded as proton decoupled spectra, and Si NMR spectra were acquired using an inverse gate pulse sequence with a relaxation delay of 30 s. Molecular weights were measured by gel permeation chromatography using a Waters Associates Model 6000A liquid chromatograph equipped with three American Polymer Standards Corp. Ultrastyragel columns in series with porosity indices of $10^3$, $10^4$, and $10^5$ Å, using freshly distilled THF as eluent. The polymer was detected with a Waters Model 440 ultraviolet absorbance detector at a wavelength of 254 nm, and the data were manipulated using a Waters Model 745 data module. Molecular weights were calibrated by polystyrene standards. Fluorescence emission and excitation spectra were recorded on a Perkin-Elmer Luminescence Spectrometer LS 50B. The solvents were determined to be free of emitting impurities prior to use. The concentration of metallole copolymers for the fluorescence quenching measurements was 10 mg/1 L, which is about $2.0 \times 10^{-6}$ M. Fluorescence spectra were taken immediately after injection of analyte. There was no change in intensity with time. The UV-vis spectra were obtained from Hewlett-Packard 8452A diode array spectrometer. Monomers, 1,1-dichloro-2,3,4,5-tetraphenylsilole, 1,1-dichloro-2,3,4,5-tetraphenylgermole, 1,1-dilithio-2,3,4,5-tetraphenylsilole, and 1,1-dilithio-2,3,4,5-tetraphenylgermole were synthesized by following the procedures described in the literature (West, R.; Sohn, H.; Bankwitz, U.; Calabrese, J.; Apelog, Y.; Mueller, T. *J. Am. Chem. Soc.* 1995, 117, 11608-11609.West, R.; Sohn, H.; Powell, D. R.; Mueller, T.; Apeloig,Y. *Angew. Chem. Int. Ed. Engl.* 1996, 35, 1002-1004. Bankwitz, U.; Sohn, H.; Powell, D. R.; West, R. *J. Organomet. Chem.* 1995, 499, C7-C9.; Sohn, H. In *New Chemistry of Siloles and Germoles, Ph. D. thesis;* University of Wisconsin: Madison, 1997, pp 1-310). These reactions were performed under an argon atmosphere.

EXAMPLE 2

Fluorescence lifetime measurements: Fluorescence decay in the range 0.05 to 20 ns was characterized by time-correlated single photon counting (TCSPC). A neodymium:vanadate laser at 530 nm (Coherent Verdi) pumped a home-built titanium:sapphire laser that generated femtosecond mode-locked pulses by self-phase-locking. Harmonic doubling provided excitation pulses near 400 nm. A portion of the beam was picked off and sent to a photodiode to provide "stop" pulses. Emission from solutions in ordinary 1 cm$^2$ luminescence cells or from solid polymer films was collected and sent through a half-meter monochromator (Spex 1870) to a microchannelplate photomultiplier (Hamamatsu 1564U-01). After amplification (Philips 774), pulses were recognized by a constant-fraction discriminator (Tennelec TC454) to provide "start" signals to the time analyzer (Canberra 2044). The "stop" pulses came from the photodiode through a separate discriminator (EGG-Ortec 934). On this occasion, pulse selection was not used. Electronic gating (Laws, W. R.; Potter; D. W.; Sutherland, J. C. *Rev. Sci. Instrum.* 1984, 55, 1564) was employed to avoid pile-up at the time analyzer. The histogram of the delay times between fluorescence and excitation was collected by a multichannel pulse height analyzer (Norland 5300) and transferred to a microcomputer for processing. The instrument response function to instantaneous emission was measured using a colloidal suspension. Deconvolution was carried out using iterative reconvolution within a least-squares routine based on the Marquardt method (Marquardt, D. W. *J. Soc. Indust. Appl. Math.* 1963, 11, 431-441) The program, developed in-house, incorporates some insights from Grinvald and Steinberg (Grinvald, A.; Steinberg, I. *Z. Anal. Biochem.* 1974, 59, 583-598). It also accommodates an infinite sequence of excitation pulses producing decays longer than the repetition period; for exponential decays, this involves only summing a simple geometric series for each fitted component. A general introduction to the methodology, along with other details of our apparatus, was provided previously (Magde, D.; Campbell, B. F. *SPEI* 1989, 1054, 61-68). However, many specifics have changed, as described above, and the main novelty described in that report, the use of in internal reference, is not currently used with the new laser system.

EXAMPLE 3

Preparation of polymetalloles (1,2): Synthesis of polygermole 2 is similar to that of polysilole 1 (Sohn, H.; Huddleston, R. R.; Powell, D. R.; West, R. *J. Am. Chem. Soc.* 1999, 121, 2935-2936.) 1,1-dichloro-2,3,4,5-tetraphenylgermole (3.0 g, 6.0 mmol) in THF (130 mL) was stirred with 2 equiv Li under Ar atmosphere. After the mixture was refluxed for three days, 4 mL of methanol was added to the reaction mixture. After removal of the solvent, the residual solid was dissolved in 5 mL of THF and then poured into 400 mL of methanol. Polygermole 2 was obtained as pale yellow powder after the third cycle of dissolving-precipitation followed by freeze-drying. 2:(1.11 g, 43%, Mw=4600, Mw/Mn=1.05, determined by SEC with polystyrene standards);$^1$H NMR(300.133 MHz, CDCl$_3$): δ=6.80-7.40 (br, m, Ph),3.60 (br, OMe);$^{13}$C{H} NMR (75.403 MHz, CDCl$_3$ (δ=77.00)): δ=125-132 (br, m, Ph)and 136-151 (br, m, germole ring carbon).

EXAMPLE 4

Preparation of silole-germole alternating copolymer 3:Stirring 1,1-dichloro-2,3,4,5-tetraphenylsilole (3.0 g, 6.6 mmol) with lithium (0.9 g, 129.7 mmol) in THF (120 mL) for 8 h at room temperature gave a dark yellow solution of silole dianion. After removal of excess lithium, 1,1-dichloro-2,3,4, 5-tetraphenylgermole (3.3 g, 6.6 mmol) was added to a solution of tetraphenylsilole dianion, and stirred at room temperature for 2 h. The resulting mixture was refluxed for 3 days. The reaction mixture was cooled to room temperature and quenched with methanol. Then, the volatiles were removed under reduced pressure. THF (20 mL) was added to the residue and polymer was precipitated by slow addition of the solution into 500 mL of methanol. The third cycle of dissolving-precipitation followed by freeze-drying gave the polymer as yellow powder. 3:(2.10 g, 39%, Mw=5500, Mw/Mn=1.10, determined by SEC with polystyrene standards);$^1$H NMR (300.133 MHz, CDCl$_3$):δ=6.30-7.40 (br, m, Ph),3.56 (br, OMe);$^{13}$C{H} NMR (75.403 MHz, CDCl$_3$(δ=77.00)): δ=125-130 (br, m, Ph)and 138-152 (br, m, silole and germole ring carbon).

EXAMPLE 5

Preparation of silole-silane copolymers, (silole-SiR$^1$R$^2$)$_n$: Stirring of 1,1-dichloro-2,3,4,5-tetraphenylsilole (5.0 g, 11.0 mmol) with lithium (0.9 g, 129.7 mmol) in THF (120 mL) for 8 h at room temperature gave a dark yellow solution of silole dianion. After removal of excess lithium, 1 mol equiv of corresponding silanes, R$^1$R$^2$SiCl$_2$(11.0 mmol) was added slowly to a solution of tetraphenylsilole dianion, and stirred at room temperature for 2 h. The resulting mixture was refluxed for 3 days. The reaction mixture was cooled to room temperature and quenched with methanol. Then the volatiles were removed under reduced pressure. THF (20 mL) was added to the residue and polymer was precipitated by slow addition of the solution into 700 mL of methanol. The third cycle of dissolving-precipitation followed by freeze-drying gave the polymer as yellow powder.

For (silole$_n$(SiMeH)$_m$(SiPhH)$_o$, each 5.5 mmol of SiMeHCl$_2$ and SiPhHCl$_2$ were slowly added into a THF solution of silole dianion. In the case of (silole-SiH$_2$)$_m$, after addition of the xylene solution of SiH$_2$Cl$_2$ (11.0 mmol), the resulting mixture was stirred for 3 days at room temperature instead of refluxing.

Selected data for (silole-SiMeH)$_n$, 4; Yield=2.10 g (44.5%); $^1$H NMR (300.134 MHz, CDCl$_3$): □=−0.88-0.60 (br. 3H, Me), 3.06-4.89 (br. 1H, Si$\underline{H}$), 6.16-7.45 (br. 20H, Ph); $^{13}$C{H} NMR (75.469 MHz, CDCl$_3$): □=0.61-1.69 (br. Me), 123.87-131.75, 137.84-145.42 (br. m, Ph), 153.07-156.73 (br. m, silole ring carbon); $^{29}$Si NMR (71.548 MHz, inversed gated decoupling, CDCl$_3$): □=−29.22 (br. silole), −66.61 (br. Si$\underline{M}$eH). GPC: Mw=4400, Mw/Mn =1.04, determined by SEC with polystyrene standards.

Selected data for (silole-SiPhH)$_n$, 5; Yield=2.00 g (37.0%); $^1$H NMR (300.134 MHz, CDCl$_3$): □=−3.00-4.00 (br. 1H, Si$\underline{H}$), 6.02-7.97 (br. 20H, Ph);
$^{13}$C{H} NMR (75.469 MHz, CDCl$_3$): □=123.64-143.98 (br. m, Ph), 152.60-157.59 (br. m, silole ring carbon); $^{29}$Si NMR (71.548 MHz, inversed gated decoupling, CDCl$_3$): □=−37.51 (br. silole), −71.61 (br. Si$\underline{P}$hH). GPC: Mw=4500, Mw/Mn=1.09, determined by SEC with polystyrene standards.

Selected data for (silole)$_n$(SiMeH)$_{0.5n}$(SiPhH)$_{0.5n}$, 6; Yield=2.10 g (41.5%);
$^1$H NMR (300.134 MHz, CDCl$_3$): □=−0.67-0.40 (br. 3H, Me), 3.08-4.98 (br. 2H, Si$\underline{H}$), 6.00-7.82 (hr. 55H, Ph); $^{13}$C{H} NMR (75.469 MHz, CDCl$_3$): □=−0.85-1.76 (br. Me), 122.06-147.25 (br. m, Ph), 153.11-157.26 (br. m, silole ring carbon); $^{29}$Si NMR (71.548 MHz, inversed gated decoupling, CDCl$_3$): □=−28.61 (br. silole), −59.88 (br. Si$\underline{M}$eH and Si$\underline{P}$hH). GPC: Mw=4800, Mw/Mn=1.16, determined by SEC with polystyrene standards.

Selected data for (silole-SiPh$_2$)$_n$, 7; Yield=2.93 g (47.0%); $^1$H NMR (300.134 MHz, CDCl$_{13}$): □=6.14-7.82 (br. 20H, Ph); $^{13}$C{H} NMR (75.469 MHz, CDCl$_3$): □=122.08-146.25 (br. m, Ph), 152.81-160.07 (silole ring carbon); GPC: Mw=5248, Mw/Mn=1.05, determined by SEC with polystyrene standards.

Selected data for (silole-SiH$_2$)$_n$, 8; Yield=2.05 g (45%); $^1$H NMR (300.134 MHz, CDCl$_3$): □=3.00-4.96 (br. 2H, Si$\underline{H}_2$), 6.12-7.72 (br. 20H, Ph); $^{13}$C{H} NMR (75.469 MHz, CDCl$_3$): □=122.08-132.78, 136.92-146.25 (br. m, Ph), 152.81-160.07 (br. m, silole ring carbon); $^{29}$Si NMR (71.548 MHz, inversed gated decoupling, CDCl$_3$): □=−30.95 (br. silole), −51.33 (br. Si$\underline{H}_2$). ratio of n:m=1.00:0.80; GPC: Mw=4600, Mw/Mn=1.14, determined by SEC with polystyrene standards.

EXAMPLE 6

Preparation of germole-silane copolymers, (germole-SiR$^1$R$^2$)$_n$: The procedure for synthesizing all germole-silane copolymers was similar to that for silole-silane copolymers. For (germole)$_n$(SiMeH)$_{0.5n}$(SiPhH)$_{0.5n}$, each 5.0 mmol of SiMeHCl$_2$ and SiPhHCl$_2$ were added slowly into a THF solution of germole dianion. The resulting mixture was stirred for 3 days at room temperature.

Selected data for (germole-SiMeH)$_n$9; Yield=2.03 g (43%); $^1$H NMR (300.134 MHz, CDCl$_3$): □=−0.21-0.45 (br. 2.4H, Me), 5.14-5.40 (br. 0.8H, Si$\underline{H}$), 6.53-7.54 (br. 20H, Ph); $^{13}$C{H} NMR (75.469 MHz, CDCl$_3$): □=−9.70-8.15 (br. Me), 125.29-130.94, 139.08-148.12 (br. m, Ph), 151.29-152.88 (br. m, germole ring carbon); $^{29}$Si NMR (71.548 MHz, inversed gated decoupling, CDCl$_3$): □=−50.40 (br. Si$\underline{M}$eH); GPC: Mw=4900, Mw/Mn=1.12, determined by SEC with polystyrene standards.

Selected data for (germole-SiPhH)$_n$ 10; Yield=2.13 g (40%); $^1$H NMR (300.134 MHz, CDCl$_3$): □=4.71 (br. 1.0H Si$\underline{H}$) 6.30-7.60 (br. 25H, Ph) $^{13}$C{H}
NMR (75.469 MHz, CDCl$_3$): □=125.50-144.50 (br. m, Ph), 151.50-153.00 (br. m, germole ring carbon); $^{29}$Si NMR (71.548 MHz, inversed gated decoupling, CDCl$_3$): □=−56.81 (br. Si$\underline{P}$hH); GPC: Mw=4400, Mw/Mn=1.06, determined by SEC with polystyrene standards.

Selected data for (germole)$_n$(SiMeH)$_{0.5n}$(SiPhH)$_{0.5n}$, 11; Yield=2.01 g (40%); $^1$H NMR (300.134 MHz, CDCl$_3$): □=−0.04-0.42 (br. 3H, Me), 4.94 (br. 2H, Si$\underline{M}$), 6.33-7.66 (br. 25H, Ph); $^{13}$C{H} NMR (75.469 MHz CDCl$_3$): □=124.31-130.66 (br. m, Ph), 138.43-152.54 (br. m, germole ring carbon); $^{29}$Si NMR (71.548 MHz, inversed gated decoupling, CDCl$_3$): □=−63.01 (br. Si$\underline{M}$eH and Si$\underline{P}$hH): 0.71; GPC: Mw=4100, Mw/Mn=1.06, determined by SEC with polystyrene standards.

Figure 17:
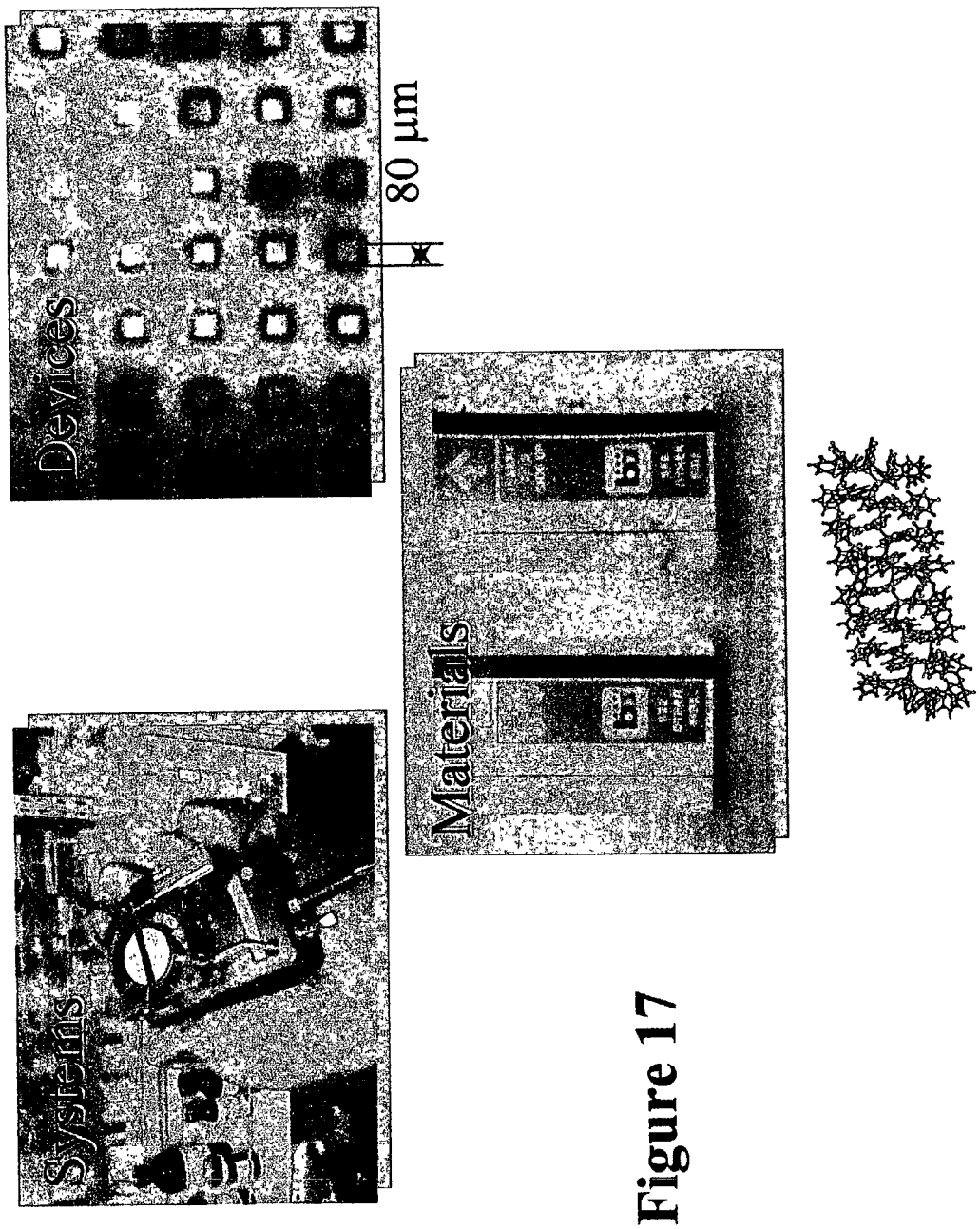
FIG. 17 shows the microsensor elements of this invention for detection of pollution, chemical agent and explosives.
Figure 18:
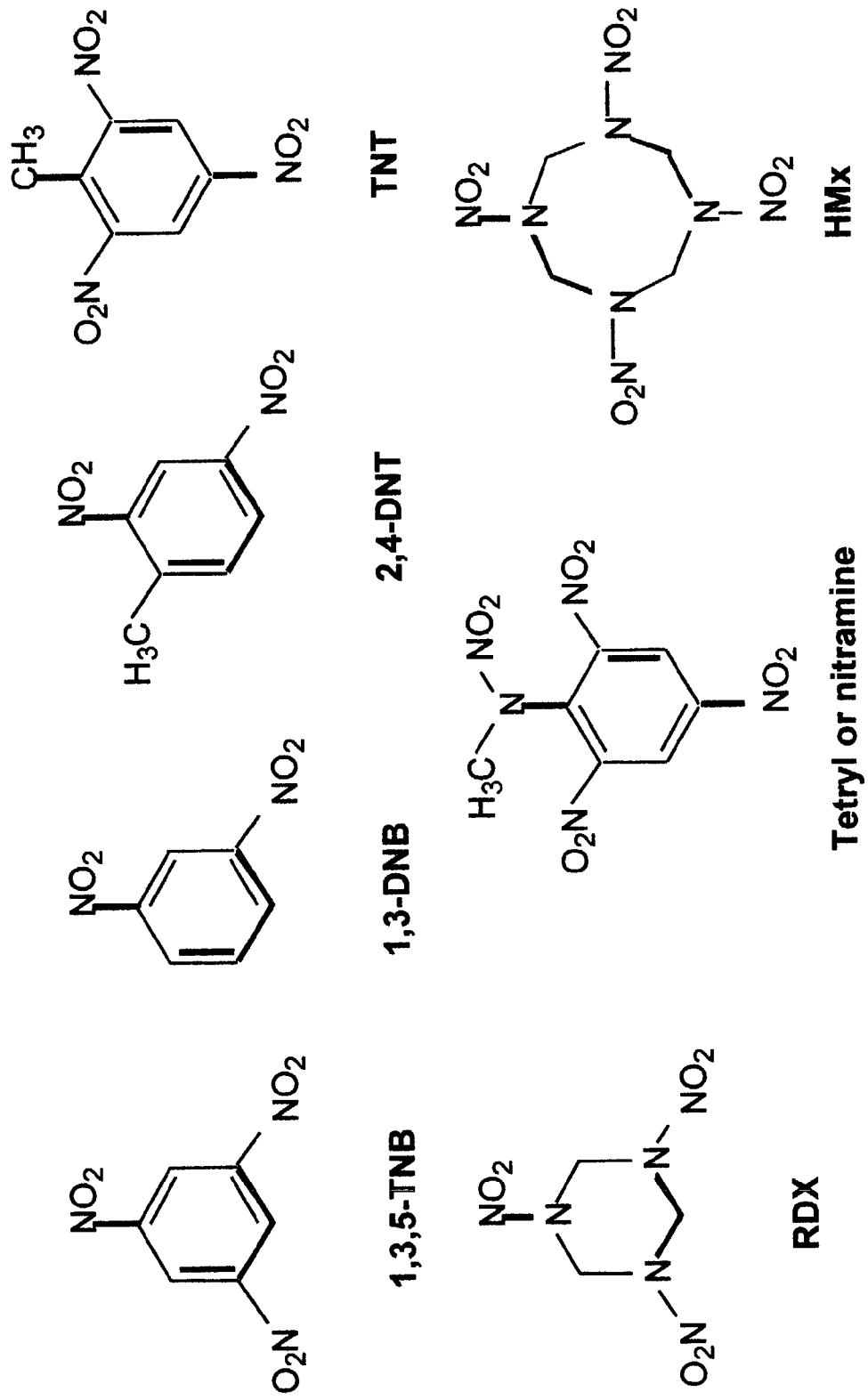
FIG. 18 illustrates the chemical Structures of Common High Explosives.

Selected data for (germole-SiPh$_2$)$_n$, 12; Yield=3.23 g (48%); $^1$H NMR (300.134 MHz, CDCl$_3$): □=6.21-7.68 (br. 30H, Ph); $^{13}$C{H} NMR (75.469 MHz, CDCl$_3$): □=125.15-141.40 (br. m, Ph), 151.12-153.99 (germole ring carbon); GPC: Mw=5377, Mw/Mn=1.09, determined by SEC with polystyrene standards. FIGS. 17-26 Text Reflecting now on the instrumentation or apparatus of this invention, FIG. 17 shows the microsensor elements of this invention for detection of pollution, chemical agent, and explosives. FIG. 18 illustrates the chemical structures of common high explosives.

Figure 19:
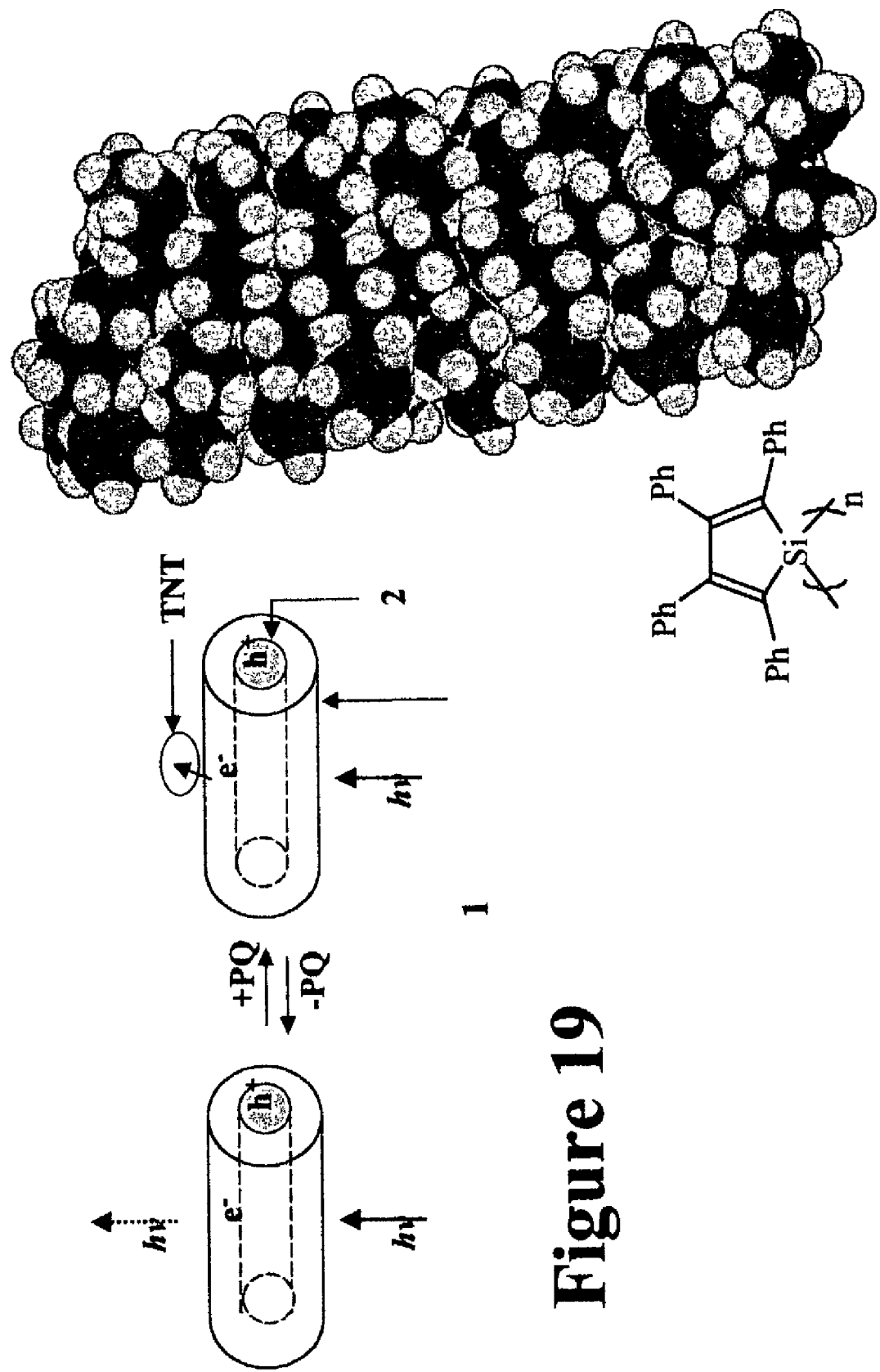
FIG. 19 is a diagrammatic representation of the Luminescent Silicon Nanowire TNT Sensors of this invention. Luminescence Quenching for sensing of Explosives and Nerve Agents. The materials operate by electron transfer quenching. Quenching is induced by an IR-emitting chromophore (for fluorophosphate nerve agent detection) or by the strongly electron-accepting class of nitroaromatic explosives (demonstrated with TNT and Picric acid).
Figure 20:
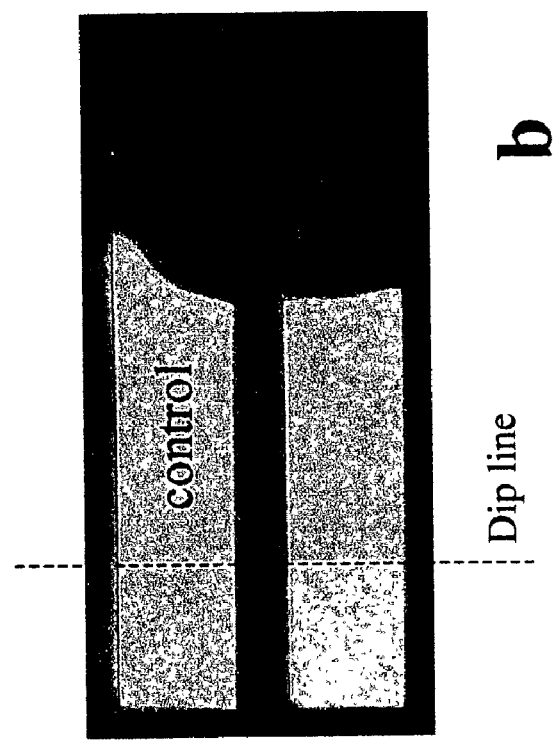
FIG. 20 are examples of results obtained by the Silicon Nanowire (Polysilole) TNT Sensors of this invention. a. A TNT-contaminated thumbprint on a transit ticket from the San Francisco BART line. The ticket on the left was not exposed to TNT and serves as a control. After exposure, the paper was coated with a fine mist of polysilole. The image was taken under a black light. b. Detection of Explosives in Seawater. Two paper tickets coated with polysilole, then soaked for 30 sec in seawater (collected off Scripps Pier, La Jolla, Calif.). The seawater used in the bottom ticket was spiked with 50 ppb of purified TNT. The top ticket is the control. The image was taken under a black light.
Figure 20:
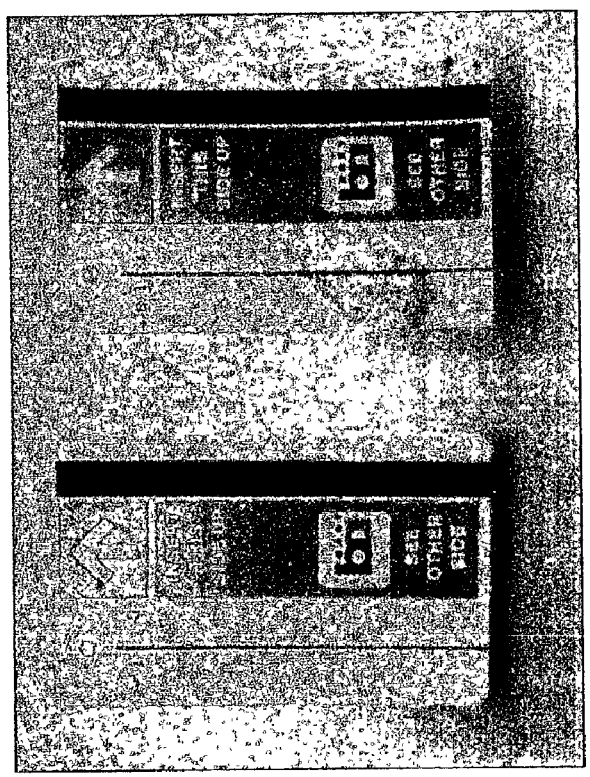

FIG. 19 is a diagrammatic representation of the luminescent silicon nanowire TNT sensors of this invention. Shown is luminescence quenching for sensing of explosives and nerve agents. The materials operate by electron transfer quenching. Quenching is induced by an IR-emitting chromophore (for fluorophosphate nerve agent detection) or by the strongly electron-accepting class of nitroaromatic explosives (demonstrated with TNT and Picric acid). FIG. 20 shows examples of results obtained by the silicon nanowire (polysilole) TNT sensors of this invention. A TNT-contaminated thumbprint on a transit ticket from the San Francisco BART line is shown at a. The ticket on the left was not exposed to TNT and serves as a control. After exposure, the paper was coated with a fine mist of polysilole. The image was taken under a black light. b. shows the detection of explosives in seawater. Two paper tickets coated with polysilole, then soaked for 30 sec in seawater (collected off Scripps Pier, La Jolla, Calif.). The seawater used in the bottom ticket was spiked with 50 ppb of purified TNT. The top ticket is the control. The image was taken under a black light.

Figure 21:
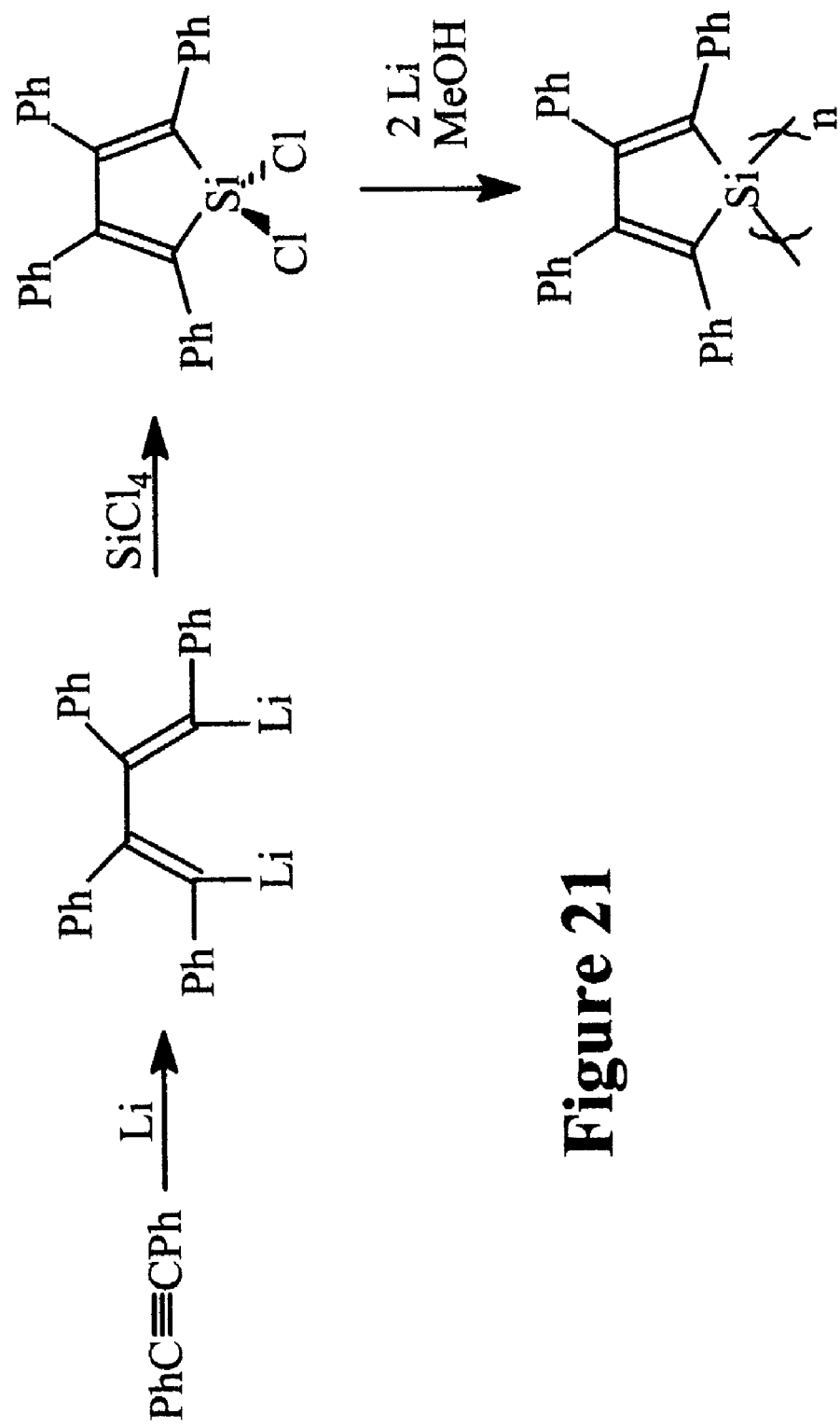
FIG. 21 demonstrates the Synthesis of Poly(Tetraphenyl-Silole). The products are highly photoluminescent polymers, soluble in organic solvents, and air and water-stable. (Yamaguchi, Y. Synthetic Met. 82, 149-153 (1996).

FIG. 21 demonstrates the synthesis of poly(tetraphenylsilole). The products are highly photoluminescent polymers, soluble in organic solvents, and air and water-stable. (Yamaguchi, Y. Synthetic Met. 82, 149-153 (1996); Tamao, K., Uchida, M., Izumizawva, T., Furukawa, K. & Yamaguchi, S. J. Am. Chem. Soc. 118, 11974-11975 (1996); Sohn, H., Huddleston, R. R., Powell, D. R. & West, R. J. Am. Chem. Soc. 121, 2935-2936 (1999)).

FIG. 22 shows Stern-Volmer Plots of the sensitivity and selectivity of the sensors of this invention in the detection of explosives (TNT, DNT, Picric Acid) in toluene.

FIG. 23 demonstrates the nanoengineered silicon sensors methodology. a. Luminescence from silicon nanodots and nanowires displays the Fabry-Perot and/or photoluminescence modes. b. Shows the workings of the transducer. FIG. 24 indicates the specificity of the sensors. a. Shows catalytic hydrolysis of cw agents. b. Right half in each frame was exposed to vapor over aqueous HF at the indicated concentrations. FIG. 25 shows a. a laser interferometer using nanocrystalline porous Si transducers. The dynamic range is 5 decades. The detection limit (ethanol) is 500 ppb. The handheld nanosensor device for nerve agent was developed by Inventors for DARPA Micro Unattended Ground Sensors program. b. A sarin run showing response to Sarin at 10 ppm within 7 min of introduction. The sampling chamber depleted of agent ca. 10 min into the run. (Dr. Kwok Ong, APGEA). FIG. 26 shows the instrumentation and results for standoff detection of VOCs with nanostructured Si photonic bandgap particles.

Conclusions and Future Prospects

The polymetalloes and metallole copolymers have been synthesized and used for the detection of explosives such as picric acid, TNT, DNT, and nitrobenzene. These polymers have similar molecular weights, which are extended oligomers with a degree of polymerization of about 10 to 16 metallole units, and show great sensitivities to the nitroaromatics. The efficiency of photoluminescence quenching is in the order of picric acid>TNT>DNT>nitrobenzene, which is correlated with their reduction potentials. This result indicates that the quenching photoluminescence properties strongly depend on the electrostatic interactions between electron rich polymers and electron deficient analytes and is primarily attributable to electron transfer from the excited metallole polymers to the LUMO of the analyte. Quenching of photoluminescence is purely a static process, since $\square_o/\square$ is invariant with quencher concentration. Each metallole polymer has a unique ratio of quenching efficiency to the corresponding analyte and each analyte has a variety of different responses to different metallole polymers, which could be utilized to specify the analyte by pattern recognition methods. These metallole copolymers are robust and insensitive to common interferents, such as organic solvent and inorganic acids. These polymetalloles and metallole copolymers exhibit 2 to 5 times better quenching efficiencies than the organic pentiptycene-derived polymer in solution. To increase the sensitivity, it may help to synthesize more elaborate metallole copolymers by changing polymer structures, or to generate longer polymer chain lengths. Sensitivity as a vapor sensor can even be improved in the solid state depending on the thickness of films (Yang, J.-S.; Swager, T. M. J. Am. Chem. Soc. 1998, 120, 5321-5322;Yang, J.-S.; Swager, T. M. J. Am. Chem. Soc. 1998, 120, 11864-11873.).

While the present invention has now been described in terms of certain preferred embodiments, and exemplified with respect thereto, one skilled in the art will readily appreciate that various modifications, changes, omissions and substitutions may be made without departing from the spirit thereof. It is intended, therefore, that the present invention be limited solely by the scope of the following claims.

REFERENCES

Albeit, K. J., Myrick, M. L., Brown, S. B., James, D. L., Milaniovich, F. P., Walt, D. R. *Envron. Sci. Technol.* 2001, 35, 3193-3200.

Albert, K. J., Lewis, N. S., Schauer, C. L., Sotzing, G. A., Stitzel, S. E., Vaid, T. P., Walt, D. R. *Chem. Rev.* 2000, 100, 2595-2626.

Alifrov, V. P., Mozjoukhine, G. V., Fisher, R. *Rev. Sci. Instrum.* 2000, 71, 1656-1659.

*Approaches for the remediation of federal facility sites contaminated with explosive or radioactive wastes.*, U.S. Environmental Protection Agency: Washington, D.C., 1993.

Bamkwitz, U., Sohn, H., Powell, D. R., West, R. *J. Organomet. Chem.* 1995, 499, C7-C9.

Barshick, S.-A. *J. Forensic Sci.* 1998, 43, 284-293.

Connors, K. A. *Binding Constants: The Measurement of Molecular Complex Stability*, Wiley-Interscience: New York, 1987.

Content, S., Trogler, W. C., Sailor, M. J. *Chem. Eur. J.* 2000, 6, 2205-2213.

Czarnik, A. W. *Nature* 1998, 394, 417-418.

Fainberg, A. *Science* 1992, 255, 1531-1537.

Freeman, W. P., Tilley, T. D., Yap, G. P. A., Rheingold, A. L. *Angew. Chem. Int. Ed. Engl.* 1996, 35, 982.

Grinvald, A., Steinberg, I. Z. *Anal. Biochem.* 1974, 59, 583-598.

Hakansson, K., Coorey, R. V., Zubarev, R. A., Talrose, V. L., Hakansson, P. *J. Mass Spectrom* 2000, 35, 337-346.

Hong, J. H., Boudjhouk, P., Castellino, S. *Organometallics* 1994, 13, 27.

Kanno, K., Ichinohe, M., Kabuto, C., Kira, M. *Chem. Lett.* 1998, 99.

Krausa, M., Schorb, K. *J. Electroanal. Chem.* 1999, 461, 10-13.

Lakowicz, J. R. *Principles of Fluorescence Spectroscopy*, Plenumn Press: New York, 1986.

Laws, W. R., Potter, D. W., Sutherland, J. C. *Rev. Sci. Instrum.* 1984, 55, 1564.

Liu, Y., Mills, R. C., Boncella, J. M., Schanze, K. S. *Langmuir* 2001, 1 7, 7452-7455.

Lu, J., Zhang, Z. *Analytica Chimica Acta* 1996, 318, 175-179.

Luggar, R. D., Farquharson, M. J., Horrocks, J. A., Lacey, R. J. *J. X-ray Spectrom,* 1998, 27, 87-94.

Magde, D., Campbell, B. F. *SPEI* 1989, 1054, 61-68.

Marquardt, D. W. *J. Soc. Indust. Appl. Math.* 1963, 11, 431-441.

McGill, R. A., Mlsna, T. E., Mowery, R. In *IEEE International Frequency Control Symposium,* 1998, pp 630-633.

McQuade, D. T., Pullen, A. E., Swager, T. M. *Chem. Rev.* 2000, 100, 2537-2574.

Rouhi, A. M. *Chem. Eng. News* 1997, 75, 14-22.

Sanji, T., Sakai, T., Kabuto, C., Sakurai, H. *J. Anm. Chem. Soc.* 1998, 120, 4552-4553.

Shriver-Lake, L. C., Donner, B. L., Ligler, F. S. *Environ. Sci. Technol.* 1997, 31, 837-841.

Sillen, A., Engelboroughs, Y. *Photochem. and Photobiol.* 1998, 67, 475-486.

Smith, K. D., McCord, B. R., McCrehan, W. A., Mount, K., Rowe, W. F. *J. Forensic Sci.* 1999, 44, 789-794.

Sohn, H., Calhoun, R. M., Sailor, M. J., Trogler, W. C. *Angew. Chem. Int. Ed. Engl.* 2001, 40, 2104-2105.

Sohn, H., Huddleston, R. R., Powell, D. R., West, R. *J. Am. Chem. Soc.* 1999, 121, 2935-2936.

Sohn, H., Trogler, W. C. manuscript submitted 2002.

Sohn, H., West, R. unpublished studies.

Sohn, H. In *New Chemistry of Siloles and Germoles, Ph. D. thesis*, University of Wisconsin: Madison, 1997, pp 1-310.

Sylvia, J. M., Janni, J. A., Klein, J. D., Spencer, K. M. Anal. Chem. 2000, 72, 5834-5840.

Tamao, K., Kawachi, A. *Adv. Organomet. Chem.* 1995, 38, 1-58.

Tamao, K., Uchida, M., Izumizawa, T., Furukawa, K., Yamaguchi, S. *J. Am. Chem. Soc.* 1996, 118, 11974-11975.

Turro, N. J. *Modern Molecular Photochemistry*, University Science Books: Sausalito, Calif., 1991.

W. H. Dennis, J., Rosenblatt, D. H., Blucher, W. G., Coon, C. L. *J. Chem. Eng. Data* 1975, 120, 202-203.

Webber, S. E. *Photochem. and Photobiol.* 1997, 65, 33-38.

West, R. In *Comprehensive Organometallic Chemistry II*, Davies, A. G., Ed., Pergamon: Oxford, 1995, pp 77-110.

West, R., Sohn, H., Powell, D. R., Mueller, T., Apeloig, Y. *Angew. Chem. Int. Ed. Engl.* 1996, 35, 1002-1004.

West, R., Sohn, H., Bankwitz, U., Calabrese, J., Apelog, Y., Mueller, T. *J. Am. Chem. Soc.* 1995, 117, 11608-11609.

Xu, Y., Fujino, T., Naito, H., Dohmaru, T., Oka, K., Sohn, H., West, R. *Jpn. J. Appl. Phys.* 1999, 38, 6915-6918.

Yamaguchi, Y. *Synthetic Met.* 1996, 82, 149-153.

Yamaguchi, S., Endo, T., Uchida, M., Izumizawa, T., Furukawa, K., Tamao, K. *Chem. Eur. J.* 2000, 6, 1683-1692.

Yamaguchi, S., Tamao, K. *Bull. Chem. Soc. Jpn.* 1996, 69, 2327-2334.

Yamaguchi, S., Jin, R., Tamao, K. *Organonmetallics* 1997, 16, 2486.

Yamaguchi, S., Tamao, K. *J. Chem. Soc., Dalton Trans.* 1998, 3693-3702.

Yang, J.-S., Swager, T. M. *J. Am. Chem. Soc.* 1998, 120, 11864-11873.

Yang, J.-S., Swager, T. M. *J. Am. Chem. Soc.* 1998, 120, 5321-5322.

What is claimed is:

1. A method for detecting electron deficient molecules in air, water or other surfaces, comprising:
   preparing photoluminescent polymetalloles;
   placing the prepared polymetalloles into a quartz flow cell containing; analytes and
   measuring the quenching of photoluminescence of the polymetallole against a standard.

2. The method of claim 1, wherein the flow cell is filled with air.

3. The method of claim 1, wherein the flow cell is filled with seawater or other liquid.

4. The method of claim 1, wherein the molecule to be detected is an explosive.

5. The method of claim 4, wherein the molecule to be detected is a member of the group consisting essentially of NB, DNT, TNT and picric acid.

6. A method for detecting explosive residue, comprising:
   preparing a silicon polymer "nanowire" sensor comprising photoluminescent polysilole;
   contacting the sensor with molecules of explosive material; and
   detecting the presence or absence of luminescence with a UV source wherein quenching of the luminescence confirms the presence of explosive.

7. The method of claim 6, wherein the sensor comprises polysilole sprayed onto a solid surface.

8. The method of claim 6, wherein the polysilole sensor is in the form of a mist that is sprayed directly onto a solid surface to be analyzed.

9. The method of claim 4, wherein the explosive material is TNT.

10. The method of claim 4, wherein the explosive material is picric acid.

11. A method for detecting an analyte that may be present in ambient air or complex aqueous media comprising:
    providing a polymer or copolymer containing a metalloid-metalloid backbone;
    exposing said polymer or copolymer to a suspected analyte or a system suspected of including the analyte; and
    measuring a quenching of photoluminescence of said polymer or copolymer exposed to the suspected analyte or the system, wherein said quenching occurs if the suspected analyte or the system contains the analyte.

12. The method of claim 11, wherein said polymer or copolymer contains tetraphenylsilole.

13. The method of claim 11, wherein said polymer or copolymer contains tetraphenylgermole.

14. The method of claim 11, wherein said metalloid-metalloid backbone is one of Si—Si, Ge—Ge, and Si'Ge.

15. The method of claim 11, wherein said step of providing a polymer or copolymer further comprises casting a thin film of said polymer or copolymer.

16. The method of claim 15 further comprising depositing said thin film on a glass substrate.

17. The method of claim 11 wherein said step of exposing said polymer or copolymer includes submerging said polymer or copolymer in an aqueous solvent.

18. The method of claim 11 wherein said step of exposing said polymer or copolymer includes submerging said polymer or copolymer in an organic solvent.

19. The method of claim 11 further comprising dissolving the polymer or copolymer in an organic solvent from the group consisting of toluene and tetrahydrofuran (THF).

20. The method of claim 11 wherein said step of measuring a quenching of photoluminescence includes subjecting said polymer or copolymer to fluorescence spectrometry.

21. The method of claim 11 wherein said step of providing said polymer or copolymer comprises dissolving said polymer or copolymer in a solvent.

22. The method of claim 11 wherein said step of providing said polymer or copolymer comprises providing a plurality of particles of said polymer or copolymer suspended in a liquid.

* * * * *

UNITED STATES PATENT AND TRADEMARK OFFICE
CERTIFICATE OF CORRECTION

PATENT NO. : 7,482,168 B2 Page 1 of 1
APPLICATION NO. : 10/244053
DATED : January 27, 2009
INVENTOR(S) : Sailor et al.

It is certified that error appears in the above-identified patent and that said Letters Patent is hereby corrected as shown below:

In Column 1, please delete lines 7-10, and insert --This invention was made with government support under Grant 9900034 awarded by National Science Foundation and Space and Naval Warfare Systems Center Contract N66001-98-C-8514 awarded by Defense Advanced Research Projects Agency (DARPA) Tactical Sensors Program. The government has certain rights in the invention.-- therefor.

In Column 1, line 39, please delete "NcQuade" and insert --"McQuade"-- therefor.

In Column 4, line 22, please delete "(silole-SiR1R2),n" and insert --(silole-SiR1R2)n,-- therefor.

In Column 5, line 50, please delete "1photoluminescence" and insert --photoluminescence-- therefor.

In Column 18, line 35, please delete "SiM" and insert --"SiH"-- therefor.

In Column 20, line 33, after "35," please delete "982" and insert --882-- therefor.

In Claim 1, Column 21, line 48, please delete "containing; analytes and" and insert --containing analytes; and-- therefor.

In Claim 14, Column 22, line 34, please delete "Si'Ge" and insert --Si-Ge-- therefor.

Signed and Sealed this

Twenty-fourth Day of March, 2009

JOHN DOLL
*Acting Director of the United States Patent and Trademark Office*